(12) United States Patent
Gudmundsson et al.

(10) Patent No.: US 7,304,068 B2
(45) Date of Patent: Dec. 4, 2007

(54) SUBSTITUTED PYRAZOLO [1,5-A] PYRIMIDINYLS AND PHARMACEUTICAL USES THEREFORE

(75) Inventors: Kristjan S Gudmundsson, Durham, NC (US); Brian A Johns, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 425 days.

(21) Appl. No.: 10/512,916

(22) PCT Filed: Apr. 30, 2003

(86) PCT No.: PCT/US03/13395

§ 371 (c)(1), (2), (4) Date: Oct. 29, 2004

(87) PCT Pub. No.: WO03/095455

PCT Pub. Date: Nov. 20, 2003

(65) Prior Publication Data

US 2005/0203106 A1 Sep. 15, 2005

Related U.S. Application Data

(60) Provisional application No. 60/379,421, filed on May 10, 2002.

(51) Int. Cl.
- A61K 31/519 (2006.01)
- C07D 487/04 (2006.01)
- A61P 31/22 (2006.01)

(52) U.S. Cl. .................... 514/259.3; 544/281

(58) Field of Classification Search ........... 544/281; 514/259.3

See application file for complete search history.

(56) References Cited

U.S. PATENT DOCUMENTS

| 5,356,897 A | 10/1994 | Oku et al. |
| 5,478,827 A | 12/1995 | Oku et al. |
| 5,624,931 A | 4/1997 | Oku et al. |
| 6,060,478 A | 5/2000 | Gilligan et al. |
| 6,124,289 A | 9/2000 | He et al. |
| 6,136,809 A | 10/2000 | Gilligan et al. |
| 6,191,131 B1 | 2/2001 | He et al. |
| 6,313,124 B1 | 11/2001 | He et al. |
| 6,358,950 B1 | 3/2002 | He et al. |
| 2003/0050320 A1 | 3/2003 | Hashimoto et al. |

FOREIGN PATENT DOCUMENTS

| EP | 0531 901 A | 3/1993 |
| JP | 2000038350 A2 | 2/2000 |
| WO | WO 96/34866 | 11/1996 |
| WO | WO 98 52937 | 11/1998 |
| WO | WO-98/54093 A1 | 12/1998 |
| WO | WO-02/16359 A | 2/2002 |
| WO | WO-02/066481 A1 | 8/2002 |

Primary Examiner—Brenda L. Coleman
Assistant Examiner—Susanna Moore
(74) Attorney, Agent, or Firm—Lorie Ann Morgan

(57) ABSTRACT

The present invention provides compounds of formula (I):

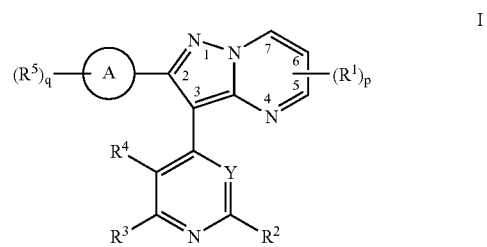

pharmaceutical compositions containing the same, processes for preparing the same and their use as pharmaceutical agents.

21 Claims, No Drawings

SUBSTITUTED PYRAZOLO [1,5-A] PYRIMIDINYLS AND PHARMACEUTICAL USES THEREFORE

CROSS REFERENCES TO RELATED APPLICATIONS

This application is a 371 Application of PCT/US03/13395, filed 30 Apr. 2003, which claims priority to U.S. application Ser. No. 60/379,421, filed 10 May 2002.

BACKGROUND OF THE INVENTION

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group are the sources of the most common viral illnesses in man. The group includes herpes simplex virus types 1 and 2 (HSV), varicelia zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. In the US alone, 40 million individuals are infected with HSV-2, a number that is expected to increase to 60 million by 2007. Over 80% of individuals infected with HSV-2 are unaware they carry and spread the virus, and of those diagnosed less than 20% received oral therapies. The net result is that less than 5% of the infected population are treated. Likewise of the 530 million individuals worldwide who carry the HSV-1 virus, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (VALTREX®) and aciclovir (ZOVIRAX®) is the standard of care for managing genital herpes virus outbreaks.

*Varicella zoster* virus (VZV) (also known as herpes zoster virus) is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atherosclerosis.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome, multiple sclerosis and Alzheimer's disease.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

BRIEF SUMMARY OF THE INVENTION

According to a first aspect of the invention there is provided a compound of formula (I):

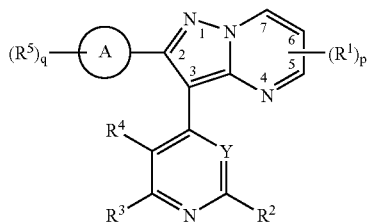

wherein:

p is 1, 2 or 3;

each $R^1$ is the same or different and is independently selected from the group consisting of halo, alkyl, alkenyl, alkynyl, cycloalkyl, cycloalkenyl, Ay, Het, —C(O)$R^9$, —C(O)Ay, —C(O)Het, —CO$_2$$R^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet, —OR$^{10}$Ay, —OR$^{10}$Het, —NR$^7$R$^8$, —NR$^7$Ay, —NHHet, —NHR$^{10}$Ay, —NHR$^{10}$Het, —S(O)$_n$R$^9$, —S(O)$_n$Ay, —S(O)$_n$Het, —S(O)$_2$NR$^7$R$^8$, —S(O)$_2$NR$^7$Ay, —R$^{10}$cycloalkyl, —R$^{10}$Ay, —R$^{10}$OR$^9$, —R$^{10}$NR$^7$R$^8$, —R$^{10}$NR$^7$Ay, —R$^{10}$NHSO$_2$R$^9$, —R$^{10}$C(O)R$^9$, —R$^{10}$C(O)Ay, —R$^{10}$C(O)Het, —R$^{10}$CO$_2$R$^9$, —R$^{10}$OC(O)R$^9$, —R$^{10}$OC(O)Ay, —R$^{10}$OC(O)Het, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$OS(O)$_n$R$^9$, cyano, nitro and azido;

each $R^7$ and $R^8$ are the same or different and are independently selected from the group consisting of H, alkyl, cycloalkyl, alkenyl, cycloalkenyl, —C(O)R$^9$, —CO$_2$R$^9$, —C(O)NR$^9$R$^{11}$, —C(S)NR$^9$R$^{11}$, —C(NH)NR$^9$R$^{11}$, —SO$_2$R$^{10}$, —SO$_2$NR$^9$R$^{11}$, —R$^{10}$cycloalkyl, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$OR$^9$, —R$^{10}$NR$^9$R$^{11}$, —R$^{10}$NHCOR$^9$, —R$^{10}$NHC(NH)NR$^9$R$^{11}$, —R$^{10}$C(NH)NR$^9$R$^{11}$, —R$^{10}$NHSO$_2$R$^9$, —R$^{10}$SO$_2$NR$^9$R$^{11}$, —R$^{10}$SO$_2$R$^{10}$ and —R$^{10}$SO$_2$NHCOR$^9$;

each $R^9$ and $R^{11}$ are the same or different and are independently selected from the group consisting of H, alkyl, cycloalkyl, —R$^{10}$cycloalkyl, —R$^{10}$OH, —R$_{10}$(OR$^{10}$)$_w$ where w is 1-10, and —R$^{10}$NR$^{10}$R$^{10}$;

each $R^{10}$ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or, 2;

Y is N or CH;

$R^2$ is selected from the group consisting of Ay, Het, —OAy, —OHet, —OR$^{10}$Ay, —OR$^{10}$Het, —NR$^7$R$^8$, —NR$^7$Ay, —NHHet, —NHR$^{10}$Ay, —NHR$^{10}$Het, —S(O)$_n$R$^9$, —S(O)$_n$Ay, —R$^{10}$NR$^7$R$^8$ and —R$^{10}$NR$^7$Ay;

$R^3$ and $R^4$ are the same or different and are each independently selected from the group consisting of H, halo, alkyl, alkenyl, cycloalkyl, Ay, Het, —C(O)R$^7$, —C(O)Ay, —CO$_2$R$^7$, —CO$_2$Ay, —OR$^7$, —OAy, —OR$^{10}$Ay, —OR$^{10}$Het, —NR$^7$R$^8$, —NR$^7$Ay, —NHHet, —SO$_2$NHR$^9$, —R$^{10}$OR$^7$, —R$^{10}$cycloalkyl, —R$^{10}$OAy, —R$^{10}$NR$^7$R$^8$ and —R$^{10}$NR$^7$Ay;

Ring A is selected from the group consisting of aryl, 5-10 membered heterocyclic group and a 5-10 membered heteroaryl group;

q is 0, 1, 2, 3, 4 or 5; and each $R^5$ is the same or different and is independently selected from the group consisting of halo, alkyl, alkenyl, alkynyl, cycloalkyl, cycloalkenyl, Ay, Het, —C(O)R$^9$, —C(O)Ay, —C(O)Het, —CO$_2$R$^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet, —OR$^{10}$Ay, —OR$^{10}$Het, —NR$^7$R$^8$, —NR$^7$Ay, —NHHet, —NHR$^{10}$Ay, —NHR$^{10}$Het, —S(O)$_n$R$^9$, —S(O)$_2$NR$^7$R$^8$, —S(O)$_2$NR$^7$Ay, —R$^{10}$cycloalkyl, —R$^{10}$Het, —R$^{10}$C(O)R$^9$, —R$^{10}$CO$_2$R$^9$, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$OR$^9$, —R$^{10}$NR$^7$R$^8$, —R$^{10}$NR$^7$Ay, —R$^{10}$SO$_2$R$^9$, —R$^{10}$SO$_2$NR$^9$R$^{11}$, —R$^{10}$SO$_2$NHCOR$^9$, cyano, nitro and azido;

or a pharmaceutically acceptable salt, solvate or physiologically functional derivative thereof.

In another aspect of the invention there is provided a pharmaceutical composition comprising a compound of formula (I). In one embodiment, the pharmaceutical composition further comprises a pharmaceutically acceptable carrier or diluent. In one embodiment, the pharmaceutical composition further comprises an antiviral agent selected from the group consisting of aciclovir and valaciclovir.

In a third aspect of the invention, there is provided a method for the prophylaxis or treatment of a herpes viral infection in an animal. The method comprises administering to the animal a therapeutically effective amount of a compound of formula (I) or a pharmaceutically acceptable salt, solvate or physiologically functional derivative thereof. The herpes viral infection can be any of herpes simplex virus 1, herpes simplex virus 2, cytomegalovirus, Epstein Barr virus, varicella zoster virus, human herpes virus 6, human herpes virus 7, and human herpes virus 8.

In a fourth aspect, there is provided a method for the prophylaxis or treatment of a condition or disease associated with a herpes viral infection in an animal. The method comprises administering to the animal a therapeutically effective amount of the compound of formula (I) or a pharmaceutically acceptable salt, solvate or physiologically functional derivative thereof.

In another aspect, there is provided a process for preparing a compound of formula (I) comprising reacting the compound of formula (VII-A):

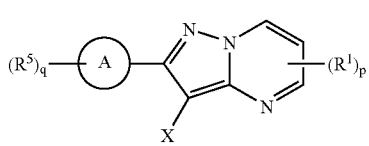

wherein X is chloro, bromo or iodo;

with a compound of formula (VIII):

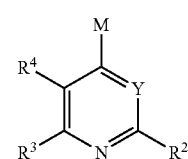

wherein M is selected from the group consisting of —B(OH)$_2$, —B(ORa)$_2$, —B(Ra)$_2$, —Sn(Ra)$_3$, Zn-halide, ZnRa, Mg-halide where Ra is alkyl or cycloalkyl and halide is halo.

In another aspect, the present invention provides a radio-labeled compound of formula (I) or a pharmaceutically acceptable salt, solvate or physiologically functional derivative thereof. In one embodiment, the present invention provides a tritiated compound of formula (I) or a pharmaceutically acceptable salt, solvate or physiologically functional derivative thereof. In another aspect, the present invention provides a biotinylated compound of formula (I) or a pharmaceutically acceptable salt, solvate or physiologically functional derivative thereof.

In another aspect, the present invention provides a compound of formula (I) for use in therapy.

In yet another aspect, the present invention provides a compound of formula (I) for use in the prophylaxis or treatment of a herpes viral infection.

In yet another aspect, the present invention provides a compound of formula (I) for use in the prophylaxis or treatment of a condition or disease associated with a herpes viral infection in an animal.

In yet another aspect, the present invention provides the use of a compound of formula (I) for the preparation of a medicament for the prophylaxis or treatment of a herpes viral infection in animal, particularly humans.

In yet another aspect, the present invention provides the use of a compound of formula (I) for the preparation of a medicament for the treatment or prophylaxis of diseases or conditions associated with a herpes viral infection in animals, preferrably humans.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as for example, compounds of formula (VII), (VI), (V) and (IV), the phrase "a compound of formula (number)" means a compound having that formula and pharmaceutically acceptable salts, solvates and physiologically functional derivatives thereof.

As used herein, the terms "alkyl" (and "alkylene") refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" also includes substituted alkyl. The alkyl groups may be optionally substituted with one or more substituents selected from the group consisting of mercapto, nitro, cyano and halo. Perhaloalkyl, such as trifluoromethyl is one particular alkyl group.

As used herein, the term "cycloalkyl" refers to a non-aromatic carbocyclic ring having from 3 to 8 carbon atoms and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may be optionally substituted on an available carbon with one or more substituents selected from the group consisting of mercapto, nitro, cyano, halo and alkyl.

As used herein, the term "alkenyl" refers to straight or branched hydrocarbon chains containing from 2 to 8 carbon atoms and at least one and up to three carbon-carbon double bonds. Examples of "alkenyl" as used herein include, but are not limited to ethenyl and propenyl. "Alkenyl" also includes substituted alkenyl. The alkenyl groups may optionally be substituted on an available carbon with one or more substituents selected from the group consisting of mercapto, nitro, cyano, halo and alkyl.

As used herein, the term "cycloalkenyl" refers to a non-aromatic carbocyclic ring having from 3 to 8 carbon atoms (unless otherwise specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on an available carbon with one or more substituents selected from the group consisting of mercapto, nitro, cyano, halo and alkyl.

As used herein, the term "alkynyl" refers to straight or branched hydrocarbon chains containing from 2 to 8 carbon atoms and at least one and up to three carbon-carbon triple bonds. Examples of "alkynyl" as used herein include, but are not limited to ethynyl and propynyl. "Alkynyl" also includes substituted alkynyl. The alkynyl groups may optionally be substituted on an available carbon with one or more substituents selected from the group consisting of mercapto, nitro, cyano, halo and alkyl.

The term "halo" or "halogen" refers to the elements fluorine, chlorine, bromine and iodine.

The term "aryl" refers to monocyclic carbocyclic groups and fused bicyclic carbocyclic groups having from 5 to 12 carbon atoms and having at least one aromatic ring. Examples of particular aryl groups include but are not limited to phenyl, and naphthyl. "Aryl" also includes substituted aryl. Aryl groups may optionally be substituted on an available carbon with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Particular aryl groups according to the invention include but are not limited to phenyl and substituted phenyl.

The term "heterocyclic" (or "heterocycle") refers to a monocyclic saturated or unsaturated non-aromatic groups and fused bicyclic non-aromatic groups, having the specified number of members and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocyclic" also includes substituted heterocyclic. The heterocyclic groups may optionally be substituted on an available carbon or heteroatom with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Particular heterocyclic groups according to the invention include but are not limited to pyrrolidine, piperidine, morpholine, thiomorpholine and piperazine and substituted variants thereof.

The term "heteroaryl" refers to aromatic monocyclic groups and aromatic fused bicyclic groups (having at least one aromatic ring) having the specified number of members and containing 1, 2, 3, or 4 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl. The heteroaryl groups may optionally be substituted on an available carbon or heteroatom with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Particular heteroaryl groups according to the invention include but are not limited to pyridine, furan, thiophene, pyrrole, imidazole, pyrazole and pyrimidine, and substituted variants thereof.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention provides compounds of formula (I):

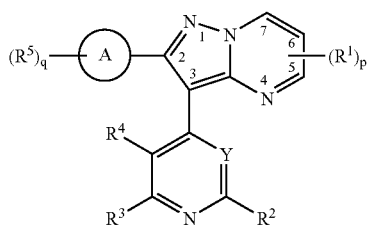

I wherein:

p is 1, 2 or 3;

each $R^1$ is the same or different and is independently selected from the group consisting of halo, alkyl, alkenyl, alkynyl, cycloalkyl, cycloalkenyl, Ay, Het, —C(O)$R^9$, —C(O)Ay, —C(O)Het, —CO$_2R^9$, —C(O)NR$^7R^8$, —C(O)NR$^7$Ay, —C(S)NR$^9R^{11}$, —C(NH)NR$^7R^8$, —C(NH)NR$^7$Ay, —O$R^7$, —OAy, —OHet, —OR$^{10}$Ay, —OR$^{10}$Het, —NR$^7R^8$, —NR$^7$Ay, —NHHet, —NHR$^{10}$Ay, —NHR$^{10}$Het, —S(O)$_nR^9$, —S(O)$_n$Ay, —S(O)$_n$Het, —S(O)$_2$NR$^7R^8$, —S(O)$_2$NR$^7$Ay, —R$^{10}$cycloalkyl, —R$^{10}$Ay, —R$^{10}$OR$^9$, —R$^{10}$NR$^7R^8$, —R$^{10}$NR$^7$Ay, —R$^{10}$NHSO$_2R^9$, —R$^{10}$C(O)$R^9$, —R$^{10}$C(O)Ay, —R$^{10}$C(O)Het, —R$^{10}$CO$_2R^9$, —R$^{10}$OC(O)$R^9$, —R$^{10}$C(O)Ay, —R$^{10}$C(O)Het, —R$^{10}$C(O)NR$^9R^{11}$, R$^{10}$C(O)NR$^7$Ay, —R$^{10}$C(O)NHR$^{10}$NR$^9R^{11}$, —R$^{10}$SO$_2$NHCOR$^9$, —R$^{10}$OS(O)$_nR^9$, cyano, nitro and azido;

each $R^7$ and $R^8$ are the same or different and are independently selected from the group consisting of H, alkyl, cycloalkyl, alkenyl, cycloalkenyl, —C(O)$R^9$, —CO$_2R^9$, —C(O)NR$^9R^{11}$, —C(S)NR$^9R^{11}$, —C(NH)NR$^9R^{11}$, —SO$_2R^{10}$, —SO$_2$NR$^9R^{11}$, —R$^{10}$cycloalkyl, —R$^{10}$C(O)$R^9$, —R$^{10}$CO$_2R^9$, —R$^{10}$C(O)NR$^9R^{11}$, —R$^{10}$C(S)NR$^9R^{11}$, —R$^{10}$OR$^9$, —R$^{10}$NR$^9R^{11}$, —R$^{10}$NHCOR$^9$, —R$^{10}$NHC(NH)NR$^9R^{11}$, —R$^{10}$C(NH)NR$^9R^{11}$, —R$^{10}$NHSO$_2R^9$, —R$^{10}$SO$_2$NR$^9R^{11}$, —R$^{10}$SO$_2R^{10}$ and —R$^{10}$SO$_2$NHCOR$^9$;

each $R^9$ and $R^{11}$ are the same or different and are independently selected from the group consisting of H, alkyl, cycloalkyl, —R$^{10}$cycloalkyl, —R$^{10}$OH, —R$^{10}$(OR$^{10}$)$_w$ where w is 1-10, and —R$^{10}$NR$^{10}R^{10}$;

each $R^{10}$ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or 2;

Y is N or CH;

$R^2$ is selected from the group consisting of Ay, Het, —OAy, —OHet, —OR$^{10}$Ay, —OR$^{10}$Het, —NR$^7R^8$, —NR$^7$Ay, —NHHet, —NHR$^{10}$Ay, —NHR$^{10}$Het, —S(O)$_nR^9$, —S(O)$_n$Ay, —R$^{10}$NR$^7R^8$ and —R$^{10}$NR$^7$Ay;

$R^3$ and $R^4$ are the same or different and are each independently selected from the group consisting of H, halo, alkyl, alkenyl, cycloalkyl, Ay, Het, —C(O)$R^7$, —C(O)Ay, —CO$_2R^7$, —CO$_2$Ay, —OR$^7$, —OAy, —OR$^{10}$Ay, —OR$^{10}$Het, —NR$^7R^8$, —NR$^7$Ay, —NHHet, —SO$_2$NHR$^9$, —R$^{10}$OR$^7$, —R$^{10}$cycloalkyl, —R$^{10}$OAy, —R$^{10}$NR$^7R^8$ and —R$^{10}$NR$^7$Ay;

Ring A is selected from the group consisting of aryl, 5-10 membered heterocyclic group and a 5-10 membered heteroaryl group;

q is 0, 1, 2, 3, 4 or 5; and each $R^5$ is the same or different and is independently selected from the group consisting of halo, alkyl, alkenyl, alkynyl, cycloalkyl, cycloalkenyl, Ay, Het, —C(O)$R^9$, —C(O)Ay, —C(O)Het, —CO$_2R^9$, —C(O)NR$^7R^8$, —C(O)NR$^7$Ay, —C(S)NR$^9R^{11}$, —C(NH)NR$^7R^8$, —C(NH)NR$^7$Ay, —O$R^7$, —OAy, —OHet, —OR$^{10}$Ay, —OR$^{10}$Het, —NR$^7R^8$, —NR$^7$Ay, —NHHet, —NHR$^{10}$Ay, —NHR$^{10}$Het, —S(O)$_nR^9$, —S(O)$_2$NR$^7R^8$, —S(O)$_2$NR$^7$Ay, —R$^{10}$cycloalkyl, —R$^{10}$Het, —R$^{10}$C(O)$R^9$, —R$^{10}$CO$_2R^9$, —R$^{10}$C(O)NR$^9R^{11}$, —R$^{10}$C(O)NR$^7$Ay, —R$^{10}$C(O)NHR$^{10}$Het, —R$^{10}$C(S)NR$^9R^{11}$, —R$^{10}$C(NH)NR$^9R^{11}$, —R$^{10}R^9$, —R$^{10}$NR$^7R^8$, —R$^{10}$NR$^7$Ay, —R$^{10}$SO$_2R^9$, —R$^{10}$SO$_2$NR$^9R^{11}$, —R$^{10}$SO$_2$NHCOR$^9$, cyano, nitro and azido;

and pharmaceutically acceptable salts, solvates and physiologically functional derivatives thereof.

In one embodiment, p is 1 or 2. In one particular embodiment, p is 1.

$R^1$ may be at the C-5, C-6 and/or C-7 positions.

Compounds of formula (I) include those compounds defined wherein at least one $R^1$ contains an aryl, heterocyclic or heteroaryl moiety. Ay, Het, —C(O)Ay, —C(O)Het, —C(O)NR$^7$Ay, —C(NH)NR$^7$Ay, —OAy, —OHet, —OR$^{10}$Ay, —OR$^{10}$Het, —NR$^7$Ay, —NHHet, —NHR$^{10}$Ay, —NHR$^{10}$Het, —S(O)$_n$Ay, —S(O)$_n$Het, —S(O)$_2$NR$^7$Ay, —R$^{10}$Ay, —R$^{10}$NR$^7$Ay, —R$^{10}$C(O)Ay, —R$^{10}$C(O)Het, —R$^{10}$OC(O)Ay, —R$^{10}$OC(O)Het, —R$^{10}$C(O)NR$^7$Ay and —R$^{10}$C(O)NHR$^{10}$Het, are examples of groups containing an aryl, heterocyclic or heteroaryl moiety. In one embodiment, the compounds of the present invention include those compounds defined wherein at least one $R^1$ contains a heterocyclic or heteroaryl moiety such as Het, —C(O)Het, —OHet, —OR$^{10}$Het, —NHHet, —NHR$^{10}$Het, —S(O)$_n$Het, —R$^{10}$C(O)Het, —R$^{10}$OC(O)Het and —R$^{10}$C(O)NHR$^{10}$Het. Another class of compounds of formula (I) includes those compounds defined wherein $R^1$ does not contain an aryl, heterocyclic or heteroaryl moiety. In this embodiment $R^1$ is typically halo, alkyl, alkenyl, alkynyl, cycloalkyl, cycloalkenyl, —C(O)$R^9$, —CO$_2R^9$, —C(O)NR$^7R^8$, —C(S)NR$^9R^{11}$, —C(NH)NR$^7R^8$, —O$R^7$, —NR$^7R^8$, —S(O)$_nR^9$, —S(O)$_2$NR$^7R^8$, —R$^{10}$cycloalkyl, —R$^{10}$O$R^9$, —R$^{10}$NR$^7R^8$, —R$^{10}$NHSO$_2R^9$, —R$^{10}$C(O)$R^9$, —R$^{10}$CO$_2R^9$, —R$^{10}$OC(O)$R^9$, —R$^{10}$C(O)NR$^9R^{11}$, —R$^{10}$C(S)NR$^9R^{11}$, —R$^{10}$C(NH)NR$^9R^{11}$, —R$^{10}$SO$_2R^9$, —R$^{10}$SO$_2$NR$^9R^{11}$, —R$^{10}$SO$_2$NHCO$R^9$, —R$^{10}$OS(O)$_nR^9$, cyano, nitro and azido. In another class of compounds of formula (1), $R^1$ does not contain a heterocyclic or heteroaryl moiety but may contain an aryl moiety. In this embodiment, $R^1$ is typically selected from the group consisting of halo, alkyl, alkenyl, alkynyl, cycloalkyl, cycloalkenyl, Ay, —C(O)$R^9$, —C(O)Ay, —CO$_2R^9$, —C(O)NR$^7R^8$, —C(O)NR$^7$Ay, —C(S)NR$^9R^{11}$, —C(NH)NR$^7R^8$, —C(NH)NR$^7$Ay, —O$R^7$, —OAy, —OR$^{10}$Ay, —NR$^7R^8$, —NR$^7$Ay, —NHR$^{10}$Ay, —S(O)$_nR^9$, —S(O)$_n$Ay, —S(O)$_2$NR$^7R^8$, —S(O)$_2$NR$^7$Ay, —R$^{10}$cycloalkyl, —R$^{10}$Ay, —R$^{10}R^9$, —R$^{10}$NR$^7R^8$, —R$^{10}$NR$^7$Ay, —R$^{10}$NHSO$_2R^9$, —R$^{10}$C(O)$R^9$, —R$^{10}$C(O)Ay, —R$^{10}$CO$_2R^9$, —R$^{10}$OC(O)$R^9$, —R$^{10}$OC(O)Ay, —R$^{10}$C(O)NR$^9R^{11}$, —R$^{10}$C(O)NR$^7$Ay, —R$^{10}$C(S)NR$^9R^{11}$, —R$^{10}$C(NH)NR$^9R^{11}$, —R$^{10}$SO$_2R^9$, —R$^{10}$SO$_2$NR$^9R^{11}$, —R$^{10}$SO$_2$NHCO$R^9$, —R$^{10}$OS(O)$_nR^9$, cyano, nitro and azido.

In one embodiment, $R^1$ is at the C-7 position.

In one embodiment, each $R^1$ is the same or different and is independently selected from the group consisting of halo, alkyl, alkenyl, alkynyl, cycloalkyl, cycloalkenyl, Ay, Het, —O$R^7$, —OAy, —OHet, —OR$^{10}$Ay, —OR$^{10}$Het, —NR$^7R^8$, —NR$^7$Ay, —NHHet, —NHR$^{10}$Ay, —NHR$^{10}$Het, —S(O)$_nR^9$, —S(O)$_n$Ay, —S(O)$_n$Het, —S(O)$_2$NR$^7R^8$ —S(O)$_2$NR$^7$Ay, cyano, nitro and azido, or any subset thereof. More particularly, each $R^1$ is the same or different and is independently selected from the group consisting of halo, Ay, Het, —NR$^7R^8$, —NHHet, —S(O)$_nR^9$, —S(O)$_n$Ay, and cyano, or any subset thereof. In one embodiment, each $R^1$ is the same or different and is independently selected from the group consisting of halo, Ay, Het and —NR$^7R^8$, or any subset thereof.

More specifically, in one embodiment, each $R^1$ may be the same or different and is independently selected from the group consisting of Cl, Ay, —NH$_2$, —NH-alkyl, —NH-cycloalkyl, —N(alkyl)(alkyl), Het, —Nalkyl-O-alkyl, and NHAy, or any subset thereof. Specific examples of some particular $R^1$ groups are selected from the group consisting of Cl, phenyl, —NH$_2$, —NH-methyl, —N(CH$_3$)$_2$, —NH-cyclopentyl, —NH-cyclopropyl, —NH-isopropyl, —NH-phenyl, —N(CH$_2$)$_2$OCH$_3$, and pyrrolidine, or any subset thereof.

In one class of compounds of formula (I), Y is CH. In another class of compounds of formula (I), Y is N.

In another embodiment, the compounds of formula (I) include those compounds defined where at least one $R^2$ contains an aryl, heterocyclic or heteroaryl moiety. A further embodiment includes those compounds of formula (I) where no $R^2$ contains a heterocyclic or heteroaryl moiety. In another embodiment, no $R^2$ contains an aryl, heterocyclic or heteroaryl moiety. From the embodiments described above with respect to $R^1$, one skilled in the art can readily determine the groups defining $R^2$ which contain or exclude aryl, heterocyclic and/or heteroaryl moieties.

In one embodiment, $R^2$ is selected from the group consisting of Het, —NR$^7R^8$, —NR$^7$Ay, —NHHet and —S(O)$_nR^9$, or any subset thereof. More particularly, $R^2$ is selected from the group consisting of Het, —NR$^7R^8$, —NR$^7$Ay and —S(O)$_nR^9$, or any subset thereof. In one embodiment, $R^2$ is selected from the group consisting of Het and —NR$^7R^8$. In another embodiment, $R^2$ is —NR$^7R^8$. In another particular embodiment, $R^2$ is —NR$^7$-cycloalkyl.

In a particular embodiment, $R^2$ is selected from the group consisting of —NH$_2$, —NH-alkyl, —NH-cycloalkyl, —N(alkyl)(alkyl), Het (e.g., pyrrolidine), —NHHet and —NH-alkyl-Het, or any subset thereof. More particularly, $R^2$ is selected from the group consisting of —NH-alkyl and —NH-cycloalkyl, or any subset thereof.

Specific examples of some particular $R^2$ groups are selected from the group consisting of —NH$_2$, —NH-methyl, —NH-ethyl, —NH-propyl, —NH-isopropyl, —NH-cyclopropyl, —NH-butyl, —NH-isobutyl, —NH-cyclobutyl, —NH-cyclopentyl, —NH-cyclohexyl, —NH(CH$_2$)$_2$OCH$_3$, and pyrrolidine (e.g., pyrrolidine bonded through N). In one embodiment, $R^2$ is —NH-cyclopentyl.

In one embodiment, $R^7$ and $R^8$ are each the same or different and are independently selected from the group consisting of H, alkyl, cycloalkyl, $R^{10}$-cycloalkyl, —R$^{10}$O$R^9$, —R$^{10}$NR$^9R^{11}$, —C(O)$R^9$, and $R^{10}$CO$_2R^9$, or any subset thereof. More particularly, $R^7$ and $R^8$ are each the same or different and are independently selected from the group consisting of H, alkyl, cycloalkyl and $R^{10}$-cycloalkyl, or any subset thereof. In one embodiment, $R^7$ and $R^8$ are each the same or different and are independently selected from the group consisting of H, alkyl and cycloalkyl or any subset thereof.

The group —R$^{10}$(OR$^{10}$)$_w$ in the definition of $R^9$ and $R^{11}$ refers to a linear PEG-like chain. In one embodiment, $R^9$ and $R^{11}$ are each the same or different and are independently selected from the group consisting of H, alkyl, cycloalkyl, and —RB$^{10}$-cycloalkyl, or any subset thereof. More particularly, $R^9$ and $R^{11}$ are each the same or different and are each independently selected from the group consisting of H and alkyl, or any subset thereof.

In one embodiment, $R^{10}$ is alkyl or cycloalkyl; more particularly alkyl.

In another embodiment, the compounds of formula (I) include those compounds defined where at least one of $R^3$ and $R^4$ contains a heterocyclic or heteroaryl moiety. A further embodiment includes those compounds of formula (I) where neither $R^3$ nor $R^4$ contain a heterocyclic or heteroaryl moiety. From the embodiments described above with respect to $R^1$, one skilled in the art can readily determine the groups defining $R^3$ and $R^4$ which contain or exclude aryl, heterocyclic and/or heteroaryl moieties.

In one embodiment, $R^3$ is selected from the group consisting of H, halo, alkyl, Ay, —O$R^7$, —CO$_2R^7$, —NR$^7R^8$, —R$^{10}$O$R^7$ and —R$^{10}$NR$^7R^8$, or any subset thereof. More particularly, $R^3$ is selected from the group consisting of H, halo, alkyl, —O$R^7$ and —NR$^7R^8$, or any subset thereof. In one particular embodiment $R^3$ is H or alkyl. In one embodiment $R^3$ is H.

In one embodiment, $R^4$ is selected from the group consisting of H, halo, alkyl, Ay, —O$R^7$, —CO$_2R^7$, —NR$^7R^8$, —R$^{10}R^7$ and —R$^{10}$NR$^7R^8$, or any subset thereof. More particularly $R^4$ is selected from the group consisting of H, halo, alkyl, $OR^7$ and $-NR^7R^8$, or any subset thereof. In one particular embodiment, $R^4$ is H or alkyl. In one embodiment $R^4$ is H.

Ⓐ in formula (I) above is herein referred to as "Ring A."

Ring A is aryl, a 5-10 membered heterocyclic group (including a 1, 2, 3 or 4 heteroatoms selected from N, O and S) or a 5-10 membered heteroaryl group (including 1, 2, 3 or 4 heteroatoms selected from N, O and S). Ring A may be bonded to the C-2 carbon of the fused ring through any suitable atom including any suitable heteroatom. In one particular embodiment, Ring A is selected from the group consisting of aryl, a 5-10 membered heterocyclic group containing 1, 2 or 3 heteroatoms selected from N, O and S and a 5-10 membered heteroaryl group containing 1, 2 or 3 heteroatom's selected from N, O and S.

In one embodiment, Ring A is selected from the group consisting of aryl, a 5-6 membered heterocyclic or heteroaryl group and a 9-membered heterocyclic or heteroaryl group. In one particular embodiment, Ring A is selected from the group consisting of aryl; a 5-6 membered heterocyclic or heteroaryl group containing 1, 2 or 3 heteroatoms selected from N, O and S; and a 9-membered heterocyclic or heteroaryl group containing 1, 2 or 3 heteroatoms selected from N, O and S.

In one embodiment, Ring A is selected from the group consisting of phenyl, naphthyl, furan, pyridine, pyrimidine, thiazole, pyrazine, pyrrole, imidazole, oxazole, benzimidazole, quinoline, isoquinoline, and quinoxoline, or any subset thereof. More particularly, Ring A in formula (I) is selected from the group consisting of phenyl, furan, pyridine and pyrimidine. In one embodiment, Ring A contains at least one N atom and is bonded through N. In another embodiment, Ring A is phenyl.

In one embodiment q is 0, 1 or 2. In one particular embodiment, q is 0. In another particular embodiment, q is 1. In one embodiment, q is 2.

$R^5$ may be in the ortho, meta and/or para position.

One class of compounds of formula (I) includes those compounds defined wherein at least one $R^5$ group contains an aryl, heterocyclic or heteroaryl moiety (in one embodiment, a heterocyclic or heteroaryl moiety). Another class of compounds of formula (I) includes those compounds defined wherein no $R^5$ group contains an aryl, heterocyclic or heteroaryl moiety (or in one embodiment no $R^5$ group contains a heterocyclic or heteroaryl moiety).

In one embodiment, each $R^5$ group is the same or different and is independently selected from the group consisting of halo, alkyl, alkenyl, Ay, Het, $-CO_2R^9$, $-C(O)NR^7R^8$, $-R^7$, $-OAy$, $-NR^7R^8$, $-NR^7Ay$, $-S(O)_2NR^7R^8$, cyano, nitro and azido, or any subset thereof. More particularly, each $R^5$ group is the same or different and is independently selected from the group consisting of halo, alkyl, alkenyl, Ay, Het, $-OR^7$, $-NR^7R^8$, $-NR^7Ay$, cyano, nitro and azido, or any subset thereof. In one particular embodiment, each $R^5$ group is the same or different and is independently selected from the group consisting of halo, alkyl, $-OR^7$, $-NR^7R^8$ and cyano, or any subset thereof.

More specifically, in one embodiment, the compounds of formula (I) are defined where each $R^5$ is the same or different and is independently selected from the group consisting of H, halo (e.g., fluoro, chloro or bromo), alkyl (e.g., methyl), O-alkyl (e.g., O-methyl, O-isobutyl, and

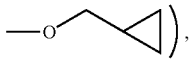

cyano, $-NH-CH_3$, and $-N(CH_3)_2$, or any subset thereof.

It is to be understood that the present invention includes all combinations and subsets of the particular groups defined hereinabove.

Specific compounds of formula (I) include but are not limited to:
3-(2-Fluoropyridin-4-yl)-2-phenyl-7-pyrrolidin-1-ylpyrazolo[1,5-α]pyrimidine;
N-Cyclopentyl-4-(2-phenyl-7-pyrrolidin-1-ylpyrazolo[1,5-α]pyrimidin-3-yl)pyridin-2-amine;
N-Cyclopentyl-3-[2-(cyclopentylamino)pyridin-4-yl]-2-phenylpyrazolo[1,5-α]pyrimidin-7-amine;
N-Cyclopentyl-3-[2-(cyclopentylamino)-4-pyridinyl]-2-(4-methoxyphenyl)pyrazolo[1,5-α]pyrimidin-7-amine;
N-Cyclopentyl-3-[2-(cyclopentylamino)-4-pyridinyl]-2-(4-fluorophenyl)pyrazolo[1,5-α]pyrimidin-7-amine; and
N-Cyclopentyl-3-[2-(cyclopentylamino)pyrimidin-4-yl]-2-(4-methoxyphenyl)pyrazolo[1,5-α]pyrimidin-7-amine,
and and pharmaceutically acceptable salts, solvates and physiologically functional derivatives thereof.

It will be appreciated by those skilled in the art that the compounds of the present invention may also be utilized in the form of a pharmaceutically acceptable salt or solvate or physiologically functional derivative thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like. In one embodiment, the compounds of formula (I) are in the form of the mesylate salt. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one, or more chiral centres are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV), Epstein Barr virus (EBV), varicella zoster virus (VZV), human herpes virus 6 (HHV-6), human herpes virus 7 (HHV-7), and human herpes virus 8 (HHV-8). Thus, the compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV infection; and multiple sclerosis which has been associated with herpes viral infections such as EBV and HHV-6. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from RFA, viral infection, particularly by CMV and/or HHV-6 of the patient plays a pivotal role in the proliferation of the smooth muscle cells in the coronary vessel treated. Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of conditions or diseases associated with hepatitis B or hepatitis C viruses, human papilloma virus (HPV) and HIV.

The present invention provides a method for the treatment or prophylaxis of a viral infection in an animal such as a mammal (e.g., a human), particularly a herpes viral infection, which method comprises administering to the animal a therapeutically effective amount of the compound of formula (I).

As used herein, the term prophylaxis refers to the prevention of infection, the prevention of occurrence of symptoms in an infected subject, the prevention of recurrence of symptoms in an infected subject, or a decrease in severity or frequency of symptoms of viral infection, condition or disease in the subject As used herein, the term "treatment" refers to the partial or total elimination of symptoms or decrease in severity of symptoms of viral infection, condition or disease in the subject, or the elimination or decrease of viral presence in the subject As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes virus infection in the subject.

The present invention also provides a method for the treatment or prophylaxis of a condition or disease associated with herpes viral infections in an animal such as a mammal (e.g., a human), which comprises administering to the animal a therapeutically effective amount of the compound of formula (I). In one embodiment, the present invention provides a method for the treatment or prophylaxis of chronic fatigue syndrome and multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome and multiple sclerosis associated with latent infection with a herpes virus.

In another embodiment, the present invention provides a method for the treatment or prophylaxis of a cardiovascular condition such as atherosclerosis, coronary artery disease or restenosis (particularly restenosis following surgery such as angioplasty), which comprises administering to the animal a therapeutically effective antiviral amount of the compound of formula (I).

The present invention further provides a method for the treatment or prophylaxis of hepatitis B or hepatitis C viruses in an animal such as a mammal (e.g., a human), which comprises administering to the animal a therapeutically effective amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the compound of formula (I) in the preparation of a medicament for the treatment of a condition or disease associated with a herpes viral infection; and the use of the compound of formula (I) in the preparation of a medicament for the treatment or prophylaxis of hepatitis B or hepatitis C viruses, human papilloma virus and HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis and atherosclerosis.

The compounds of formula (I) are conveniently administered in the form of pharmaceutical compositions. Such compositions may conveniently be presented for use in conventional manner in admixture with one or more physiologically acceptable carriers or diluents.

While it is possible that compounds of the present invention may be therapeutically administered as the raw chemical, it is common to present the active ingredient as a pharmaceutical formulation or composition. The pharmaceutical composition may comprise a pharmaceutically acceptable carrier or diluent The carrier(s) or diluent(s) must be "acceptable" in the sense of being compatible with the other ingredients of the formulation and not deleterious to the recipient thereof.

Accordingly, the present invention further provides for a pharmaceutical formulation or composition comprising a compound of formula (I). In one embodiment, the pharmaceutical composition further comprises one or more pharmaceutically acceptable carriers or diluents and optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association the compound(s) ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules (including soft-gel capsules), cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent The tablets may optionally be coated or scored and may be formulated so as to provide slow or controlled release of the active ingredient therein. The tablets may be coated according to methods well-known in the art Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides. Liquid preparations may also be formulated as soft-gel capsules for oral administration, e.g., containing conventional soft-gel excipients such as polyethylene glycol.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described. Formulations for rectal administration may be presented as a suppository with the usual carriers such as cocoa butter, hard fat or polyethylene glycol.

Formulations suitable for topical (e.g., dermal) or intra-nasal application include ointments, creams, lotions, pastes, gels, sprays, aerosols and oils. Suitable carriers for such formulations include petroleum jelly, lanolin, polyethyleneglycols, alcohols, and combinations thereof.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02-5000 mg per day, particularly 100-1500 mg per day. The desired dose may conveniently be presented in a single dose or as divided doses administered at appropriate intervals, for example as two, three, four or more sub-doses per day. The formulations according to the invention may contain between 0.1-99% of the active ingredient, conveniently from 30-95% for tablets and capsules and 3-50% for liquid preparations.

The compound of formula (I) for use in the instant invention may be used in combination with other therapeutic agents for example, non-nucleotide reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, fameyclovir, gancyclovir, docosanol, miribavir, amprenavir, lamivudine, zidovudine, and abacavir and pharmaceutically acceptable salts or solvates thereof. Particular antiviral agents for combining with the compounds of the present invention include aciclovir and valaciclovir and pharmaceutically acceptable salts or solvates thereof. Thus the present invention provides in a further aspect, a combination comprising a compound of formula (I) and an antiviral agent selected from the group consisting of aciclovir and valaciclovir and pharmaceutically acceptable salts or solvates thereof; the use of such combination in the treatment of viral infections and the preparation of a medicament for the treatment of viral infections, and a method of treating viral infections comprising administering a compound of formula (I) and an antiviral agent selected from the group consisting of aciclovir and valaciclovir and pharmaceutically acceptable salts or solvates thereof.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art.

Compounds of formula (I) wherein p is 1 and $R^1$ is selected from the group consisting of Het, —$OR^7$, —OAy, —OHet, —$OR^{10}$Ay, —$OR^{10}$Het, —$NR^7R^8$, —$NR^7$Ay, —NHHet, —$NHR^{10}$Ay, —$NHR^{10}$Het, —$S(O)_nR^9$, —$S(O)_n$Ay, —$S(O)_n$Het and azido, may be conveniently prepared by the process outlined in Scheme 1 below.

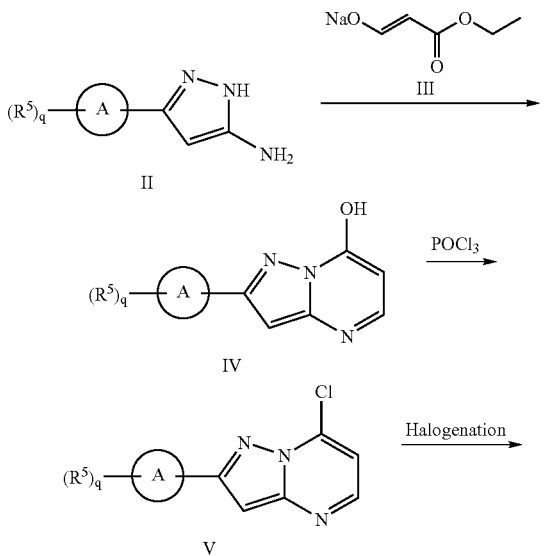

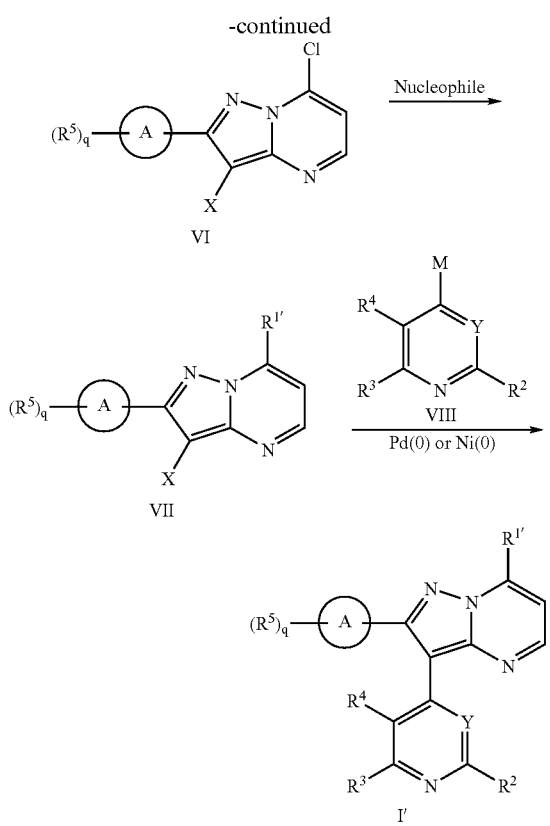

wherein:

p is 1;

R$^{1'}$ is selected from the group consisting of Het, —OR$^7$, —OAy, —OHet, —OR$^{10}$Ay, —OR$^{10}$Het, —NR$^7$R$^8$, —NR$^7$Ay, —NHHet, —NHR$^{10}$Ay, —NHR$^{10}$Het, —S(O)$_n$R$^9$, —S(O)$_n$Ay, —S(O)$_n$Het and azido;

each R$^7$ and R$^8$ are the same or different and are independently selected from the group consisting of H, alkyl, cycloalkyl, alkenyl, cycloalkenyl, —C(O)R$^9$, —CO$_2$R$^9$, —C(O)NR$^9$R$^{11}$, —C(S)NR$^9$R$^{11}$, —C(NH)NR$^9$R$^{11}$, —SO$_2$R$^{10}$, —SO$_2$NR$^9$R$^{11}$, —R$^{10}$cycloalkyl, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$OR$^9$, —R$^{10}$NR$^9$R$^{11}$, —R$^{10}$NHCOR$^9$, —R$^{10}$NHC(NH)NR$^9$R$^{11}$, —R$^{10}$C(NH)NR$^9$R$^{11}$, —R$^{10}$NHSO$_2$R$^9$, —R$^{10}$SO$_2$NR$^9$R$^{11}$, —R$^{10}$SO$_2$R$^{10}$ and —R$^{10}$SO$_2$NHCOR$^9$;

each R$^9$ and R$^{11}$ are the same or different and are independently selected from the group consisting of H, alkyl, cycloalkyl, —R$^{10}$cycloalkyl, —R$^{10}$OH, —R$^{10}$(OR$^{10}$)$_w$ where w is 1-10, and —R$^{10}$NR$^{10}$R$^{10}$;

each R$^{10}$ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or 2;

Y is N or CH;

R$^2$ is selected from the group consisting of Ay, Het, —OAy, —OHet, —OR$^{10}$Ay, —OR$^{10}$Het, —NR$^7$R$^8$, —NR$^7$Ay, —NHHet, —NHR$^{10}$Ay, —NHR$^{10}$Het, —S(O)$_n$R$^9$, —S(O)$_n$Ay, —R$^{10}$NR$^7$R$^8$ and —R$^{10}$NR$^7$Ay;

R$^3$ and R$^4$ are the same or different and are each independently selected from the group consisting of H, halo, alkyl, alkenyl, cycloalkyl, Ay, Het, —C(O)R$^7$, —C(O)Ay, —CO$_2$R$^7$, —CO$_2$Ay, —OR$^7$, —OAy, —OR$^{10}$Ay, —OR$^{10}$Het, —NR$^7$R$^8$, —NR$^7$Ay, —NHHet, —SO$_2$NHR$^9$, —R$^{10}$OR$^7$, —R$^{10}$cycloalkyl, —R$^{10}$OAy, —R$^{10}$NR$^7$R$^8$ and —R$^{10}$NR$^7$Ay;

Ring A is selected from the group consisting of aryl, 5-10 membered heterocyclic group and a 5-10 membered heteroaryl group;

q is 0, 1, 2, 3, 4 or 5;

each R$^5$ is the same or different and is independently selected from the group consisting of halo, alkyl, alkenyl, alkynyl, cycloalkyl, cycloalkenyl, Ay, Het, —C(O)R$^9$, —C(O)Ay, —C(O)Het, —CO$_2$R$^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet, —OR$^{10}$Ay, —OR$^{10}$Het, —NR$^7$R$^8$, —NR$^7$Ay, —NHHet, —NHR$^{10}$Ay, —NHR$^{10}$Het, —S(O)$_n$R$^9$, —S(O)$_2$NR$^7$R$^8$, —S(O)$_2$NR$^7$Ay, —R$^{10}$cycloalkyl, —R$^{10}$Het, —R$^{10}$C(O)R$^9$, —R$^{10}$CO$_2$R$^9$, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$OR$^9$, —R$^{10}$NR$^7$R$^8$, —R$^{10}$NR$^7$Ay, —R$^{10}$SO$_2$R$^9$, —R$^{10}$SO$_2$NR$^9$R$^{11}$, —R$^{10}$SO$_2$NHCOR$^9$, cyano, nitro and azido;

X is Cl, Br or I; and

M is —B(OH)$_2$, —B(ORa)$_2$, —B(Ra)$_2$, —Sn(Ra)$_3$, Zn—halide, ZnRa, Mg—halide where Ra is alkyl or cycloalkyl and halide is halo.

Generally, the process for preparing the compounds of formula (I) wherein p is 1 and R$^1$ is selected from the group consisting of Het, —OR$^7$, —OAy, —OHet, —OR$^{10}$Ay, —OR$^{10}$Het, —NR$^7$R$^8$, —NR$^7$Ay, —NHHet, —NHR$^{10}$Ay, —NHR$^{10}$Het, —S(O)$_n$R$^9$, —S(O)$_n$Ay, —S(O)$_n$Het and azido, (all formulas and all other variables having been defined above in connection with Scheme 1) comprises the steps of:

a) reacting an aminopyrazole of formula (II) with a sodium salt of ethylformyl acetate of formula (III) to prepare a compound of formula (IV);

b) treating the compound of formula (IV) with a chlorinating-dehydrating agent to prepare a compound of formula (V);

c) halogenating the compound of formula (V) to prepare a compound of formula (VI);

d) reacting the compound of formula (VI) with a nucleophile selected from the group consisting of Het, —OR$^7$, —OAy, —OHet, —OR$^{10}$Ay, —OR$^{10}$Het, —NR$^7$R$^8$, —NR$^7$Ay, —NHHet, —NHR$^{10}$Ay, —NHR$^{10}$Het, —S(O)$_n$R$^9$, —S(O)$_n$Ay, —S(O)$_n$Het and azido, to prepare a compound of formula (VII); and e) reacting the compound of formula (VII) with a compound of formula (VIII) to prepare a compound of formula (I').

More specifically, a compound of formula (I) wherein p is 1 and R$^1$ is selected from the group consisting of Het, —OR$^7$, —OAy, —OHet, —OR$^{10}$Ay, —OR$^{10}$Het, —NR$^7$R$^8$, —NR$^7$Ay, —NHHet, —NHR$^{10}$Ay, —NHR$^{10}$Het, —S(O)$_n$R$^9$, —S(O)$_n$Ay, —S(O)$_n$Het and azido (i.e., a compound of formula (I'), can be prepared reacting the compound of formula (VII) with a compound of formula (VIII):

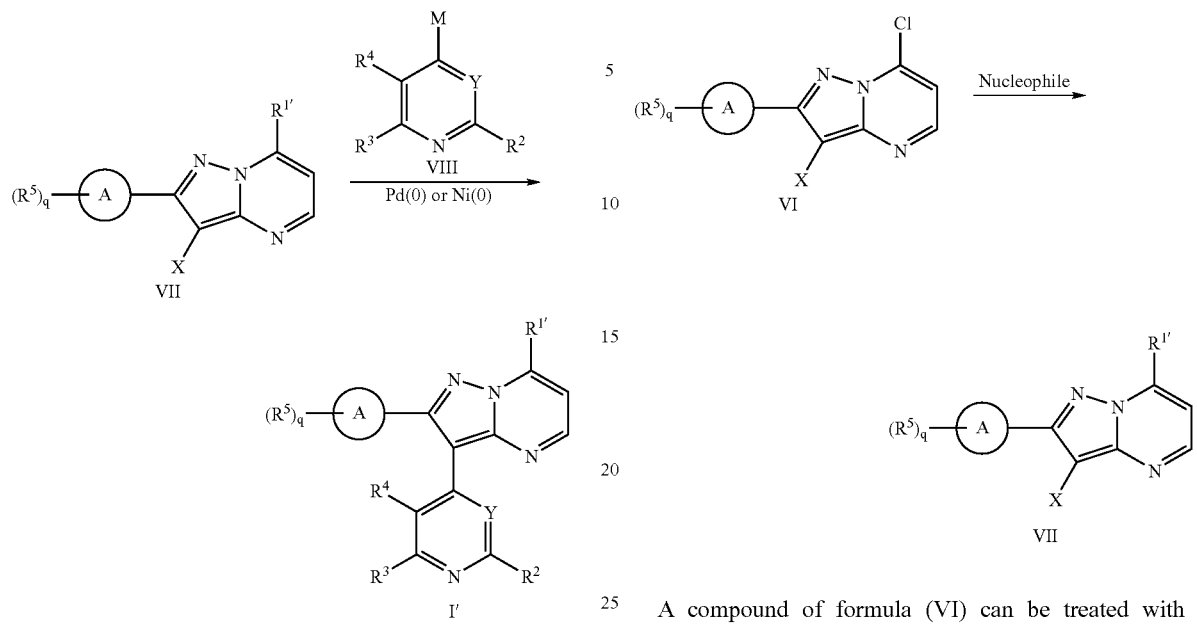

where all variables are as defined above in connection with Scheme 1.

The reaction may be carried out in an inert solvent, in the presence of a palladium (0) or nickel (0) catalyst. The reaction may optionally be heated to about 50-150° C. Typically the reaction is performed by reacting equimolar amounts of a compound of formula (VII) with a Het-metal compound of formula (VIII), but the reaction may also be performed in the presence of an excess of the compound of formula (VIII). The palladium or nickel catalyst is typically present in 1-10 mol % compared to the compound of formula (VII). Examples of suitable palladium catalysts include but are not limited to, tetrakis(triphenylphosphine) palladium (0), dichlorobis(triphenyl-phosphine)palladium (II), tris(dibenzylideneacetone)dipalladium (0), and bis (diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the Het-metal compound of formula (VIII) is an arylboronic acid or ester or an arylboronate the reaction is more conveniently carried out by adding a base in a proportion equivalent to, or greater than, that of the compound of formula (VII). Het-metal compounds of formula (VIII) may be obtained from commercial sources or prepared either as discreet isolated compounds or generated in situ using methods known to one skilled in the art. (Suzuki, A. *J. Organomet Chem*. 1999, 576, 147; Stille, J. *Angew. Chem. Int. Ed. Engl*. 1986, 25, 508; Snieckus, V. *J. Org. Chem*. 1995, 60, 292).

A compound of formula (VII) can be prepared by reacting a compound of formula (VI) with a suitable nucleophile to provide compounds of formula (VII) wherein $R^{1'}$ is selected from the group consisting of Het, —$OR^7$, —OAy, —OHet, —$OR^{10}$Ay, —$OR^{10}$Het, —$NR^7R^8$, —$NR^7$Ay, —NHHet, —$NHR^{10}$Ay, —$NHR^{10}$Het, —$S(O)_nR^9$, —$S(O)_n$Ay, —$S(O)_n$Het and azido.

A compound of formula (VI) can be treated with a nucleophile neat or the reaction can be carried out in an inert solvent at room temperature or optionally with heating to provide compound of formula (VII). Appropriate nucleophiles for substituting the group $R^{1'}$ on the ring will be apparent to those skilled in the art of organic synthesis.

A compound of formula (VI) can be prepared from a compound of formula (V) via a halogenation procedure.

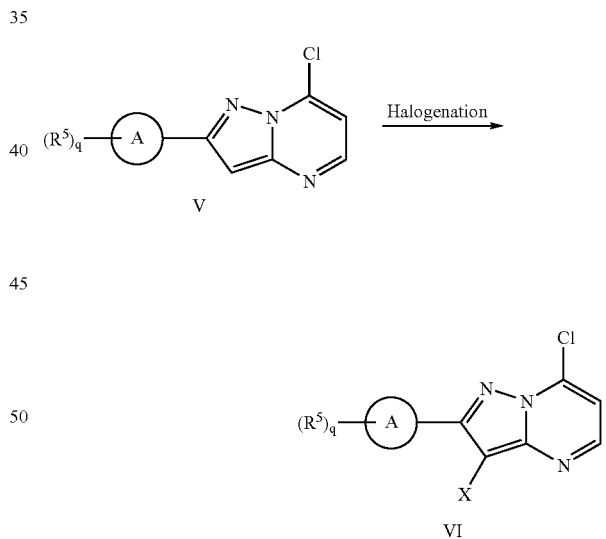

Typically, the halogenation reaction is carried out by treating the compounds of formula (V) with a halogenating agent in a suitable solvent. Suitable halogenating agents include but are not limited to, N-bromosuccinimide, trialkylammonium tribromides, bromine, N-chlorosuccinimide, N-iodosuccinimide, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, and the like.

A compound of formula (V) can be prepared from a compound of formula (IV).

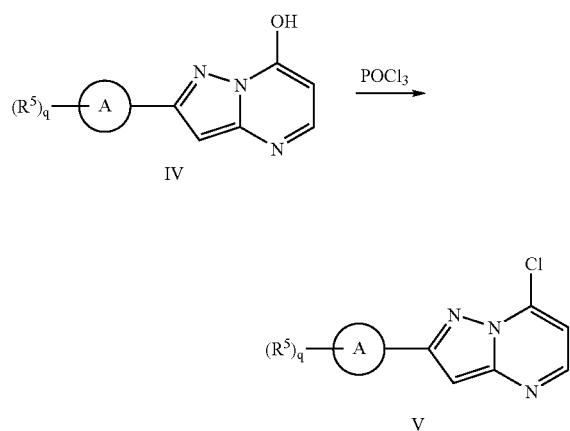

Conveniently, this type of transformation can be carried out using phosphorous oxychloride, optionally in the presence of a base. This is performed by treating a compound of formula (IV) with phosphorous oxychloride with optional heating. Typically an excess of the dehydrating reagent is used and the reaction can be heated up to reflux temperature of approximately 105° C. By way of example a particular base is N,N-diethylaniline and the like.

A compound of formula (IV) can be prepared from a compound of formula (II).

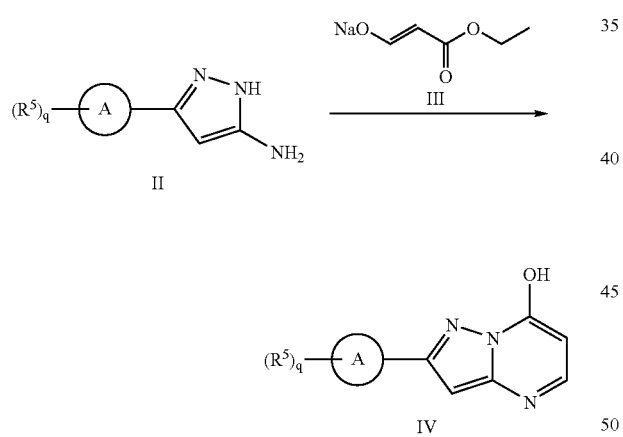

Treatment of the aminopyrazole of formula (II) with sodium salt of ethyl formylacetate of formula (III) (prepared from ethyl acetate and ethyl formate as described in J. Am. Chem. Soc. 1903, 29, 478) in a suitable solvent with heating gives a compound of formula (IV). An example of a suitable solvent is ethyl alcohol. Compounds of formula (II) are either commercially available or can be prepared by methods known to those skilled in the art of organic synthesis.

In addition to the foregoing methods of synthesis, the compounds of formula (I) and pharmaceutically acceptable salts, solvates and physiologically functional derivatives thereof may also be prepared using procedures analogous to those described in PCT Publication No. WO02/16359, published to GlaxoSmithKline Inc., the disclosure of which is incorporated herein by reference in its entirety.

The preparation of compounds of formula (I) wherein the pyrazolo[1,5-α]pyrimidines are substituted at the C-7 position is shown in Scheme 1. Compounds of formula (I) wherein the pyrazolo[1,5-α]pyrimidines exhibit a different substitution pattern at C5, C-6 and C-7 can be obtained using procedures analogous to those described in Scheme 1 above and by adaptation of procedures found in the literature (e.g., COMPREHENSIVE HETEROCYCLIC CHEMISTRY, Katritzky A. R. and Rees, C. W. (Eds), 1984, volume 5).

For example, condensation of an aminopyrazole with malonimidate gives 5,7-diaminosubstituted pyrazolo[1,5-α] pyrimidines (Arch. Pharm. 1985, 318:87-88) that can be elaborated into compounds of formula (I) using conditions similar to those in Scheme 1. Other disubstituted derivatives can be obtained as described in the literature (Farmaco, 1978, 33:14-20) and elaborated into compounds of formula (I) using the procedures described in Scheme 1 above.

In particular, the palladium or nickel coupling reaction of the pyrazolo[1,5-α]pyrimidine with the compound of formula (VII) can be accomplished with pyrazolo[1,5-α]pyrimidines having any of various substitutions represented by $(R^1)_p$ in formula (I). Hence, the present invention also provides a process for preparing compounds of formula (I) which process comprises reacting a compound of formula (VII-A) with a compound of formula (VIII)

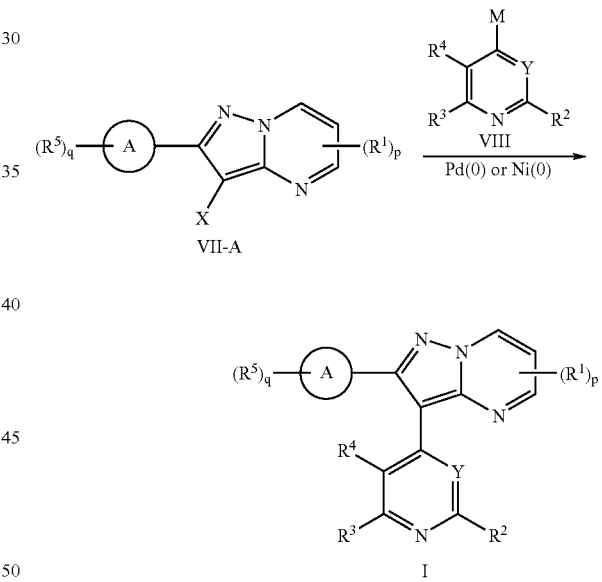

wherein p and $R^1$ are as defined in connection with compounds of formula (I) above and and all variables are defined as in Scheme 1.

As will be apparent to those skilled in the art, a compound of formula (I) may be converted to another compound of formula (I) using techniques well known in the art. For example, one method of converting a compound of formula (I) to another compound of formula (I) comprises a) oxidizing the compound of formula (I-A) to prepare a compound of formula (I-B) and then b) optionally reacting a compound of formula (I-B) with an oxygen or amine nucleophile selected from the group consisting of Het bonded through N, —$OR^7$, —OAr, —OHet, —$OR^{10}$Het, —$NR^7R^8$, —NHHet, —$NHR^{10}$Ay and —$NHR^{10}$Het to produce a compound of formula (I) wherein $R^2$ is selected from the group consisting of Het bonded through N, —OR⁷, —OAr, —OHet, —OR¹⁰Het, —NR⁷R⁸, —NHHet, —NHR¹⁰Ay and —NHR¹⁰Het.

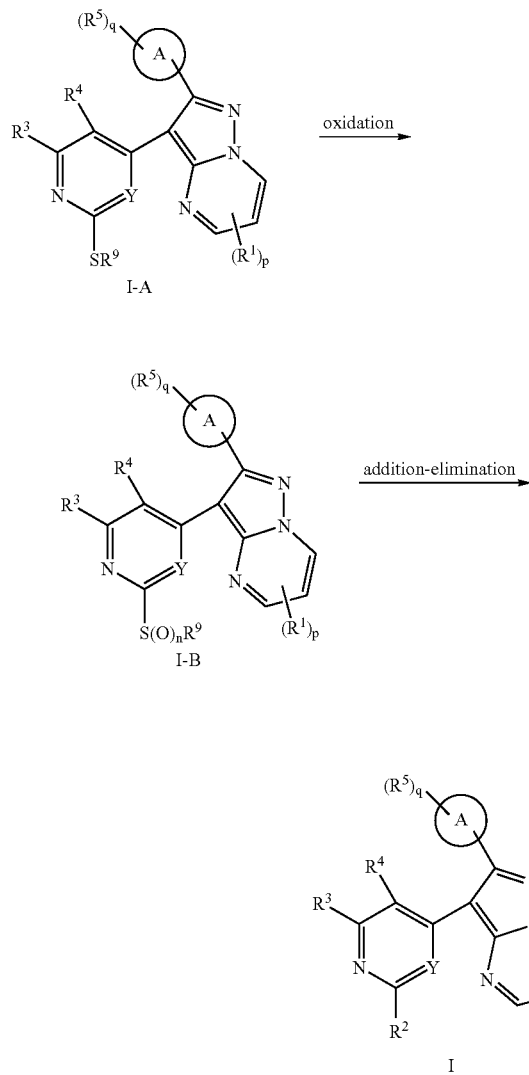

wherein R² is selected from the group consisting of Het bonded through N, —OR⁷, —OAr, —OHet, —OR¹⁰Het, —NR⁷R⁸, —NHHet, —NHR¹⁰Ay and —NHR¹⁰Het, n' is 1 or 2; and all other variables are as above.

More specifically, a compound of formula (I) can be prepared by reacting a compound of formula (I-B) (i.e., a compound of formula (I) wherein R² is —S(O)$_{n'}$R⁹ where n' is 1 or 2) with an oxygen or amine nucleophile selected from the group consisting of Het bonded through N, —OR⁷, —OAr, —OHet, —OR¹⁰Het, —NR⁷R⁸, —NHHet, —NHR¹⁰Ay and —NHR¹⁰Het. The reaction may be carried out neat or in a suitable solvent and may be heated to 50-150° C. Typically the solvent is a lower alcohol such as methanol, ethanol, isopropanol and the like or solvent such as N,N-dimethylformamide or tetrahydrofuran, and the like. Optionally a base may be used to facilitate the reaction. Typically the base can be potassium carbonate, or an amine base such as triethylamine.

A compound of the formula (I-B) may be conveniently prepared by reacting a compound of formula (I-A) (i.e., a compound of formula (I) wherein R² is —S(O)$_n$R⁹ where n is 0) with an oxidizing agent in an inert solvent, optionally in the presence of a base. Typically the oxidizing agent is a peracid such as m-chloroperbenzoic acid or the like optionally with a base such as sodium bicarbonate. Careful monitoring of the stoichiometry between the oxidizing agent and the substrate allows the product distribution between sulfoxide (n=1), and sulfone (n=2) to be controlled. Suitable solvents include but are not limited to, dichloromethane, chloroform and the like.

Another particularly useful method for converting a compound of formula (I) to another compound of formula (I) comprises reacting a compound of formula (I-C) (i.e., a compound of formula (I) wherein R² is fluoro) with an amine nucleophile (including substituted amines, heterocycles and heteroaryls, particularly those linked through N), and optionally heating the mixture to 50-150° C. to prepare a compound of formula (I-D) (i.e., a compound of formula (I) wherein R²' is selected from the group consisting of Het, —NR⁷R⁸, —NHHet, —NHR¹⁰Ay and —NHR¹⁰Het).

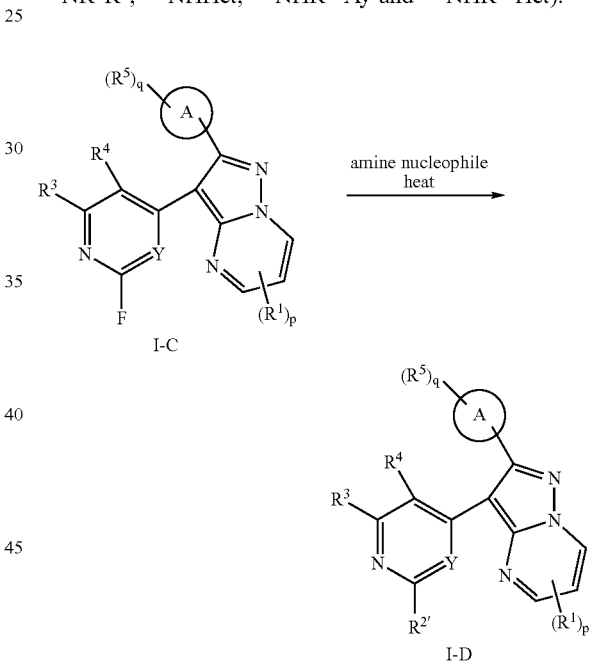

wherein R²' is selected from the group consisting of Het, —NR⁷R⁸, —NHHet, —NHR¹⁰Ay, and —NHR¹⁰Het all other variables are as defined above.

This procedure may be carried out by mixing a compound of formula (I-C) in a neat amine, or in a suitable solvent with an excess of amine to produce a compound of formula (I-D). Typically the solvent is a lower alcohol such as methanol, ethanol, isopropanol or the like. Other suitable solvents may include N,N-dimethyl-formamide, 1-methyl-2-pyrrolidine and the like.

As a further example, a compound of formula (I-E) (i.e., where X¹ is halogen) may be converted to a compound of formula (I-F) using amination techniques known to those skilled in the art.

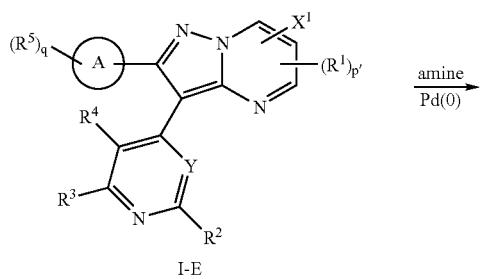

I-E

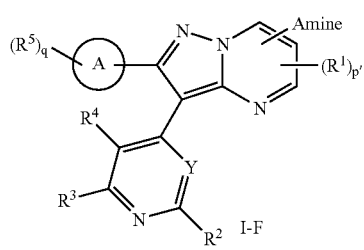

I-F wherein:

$X^1$ is halo, such as chloro, bromo or iodo;

Amine is selected from the group consisting of Het bonded through N, —$NR^7R^8$, —NHHet, —$NHR^{10}$Ar and —$NHR^{10}$Het;

p' is 0, 1 or 2.

and all other variables are as defined above.

The reaction can be carried out via an adaptation of procedures found in the literature (Wolfe, J. P.; Buchwald, S. L. *J. Org. Chem.* 2000, 65,1144) wherein a compound of the formula (I-E) is treated with an amine, a palladium (0) or nickel (0) source and a base, optionally in a suitable solvent, at a temperature ranging from ambient temperature to 200 °C. Suitable sources of palladium (0) include but are not limited to palladium(II) acetate and tris(dibenzylideneacetone) dipalladium (0). Typical bases for use in the reaction include, for example sodium tert-butoxide and cesium carbonate.

The reaction can be carried out in neat amine or in a suitable solvent. Toluene is an example of a suitable solvent As a further example, a compound of formula (I-G) (i.e., a compound of formula (I) wherein q is 1 or more and at least one $R^5$ is —O-methyl) may be converted to a compound of formula (I-H) (i.e., a compound of formula (I) wherein q is 1 or more and at least one $R^5$ is —OH) using conventional demethylation techniques. Additionally, a compound of formula (I-H) may optionally be converted to a compound of formula (I-J) (i.e., a compound of formula (I) wherein q is 1 or more and at least one $R^5$ is —$OR^{10}$). For example, the foregoing conversions are represented schematically as follows:

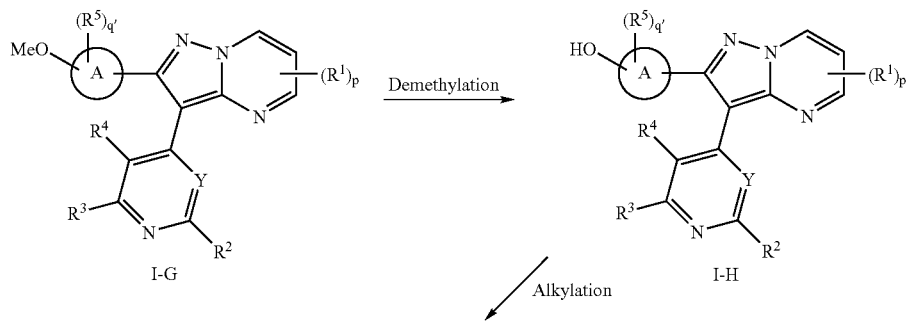

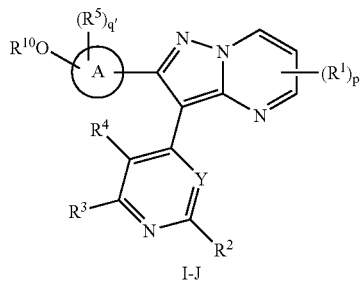

I-J wherein q' is 1, 2 or 3; Me is methyl, and all other variables are as defined above.

The demethylation reaction may be carried out by treating a compound of formula (I-G) in a suitable solvent with a Lewis acid at a temperature of –78° C. to room temperature, to produce a compound of formula (I-H). Typically the solvent is an inert solvent such as dichloromethane, chloroform, acetonitrile, toluene or the like. The Lewis acid may be boron tribromide, trimethylsilyl iodide and the like.

at least one $R^5$ is halo) or a compound of formula (I-M) (i.e. a compound of formula (I) wherein q is 1 or more and at least one $R^5$ is nitro) can be converted to a compound of formula (I-L) (i.e., a compound of formula (I) wherein q is 1 or more and at least one $R^5$ is —$NH_2$). Optionally, a compound of formula (I-L) may then be converted to a compound of formula (I-N) (i.e., a compound of formula (I) wherein q is 1 or more and at least one $R^5$ is —$NR^7R^8$ where $R^7$ and $R^8$ are not both H). For example, the foregoing conversions are represented schematically as follows:

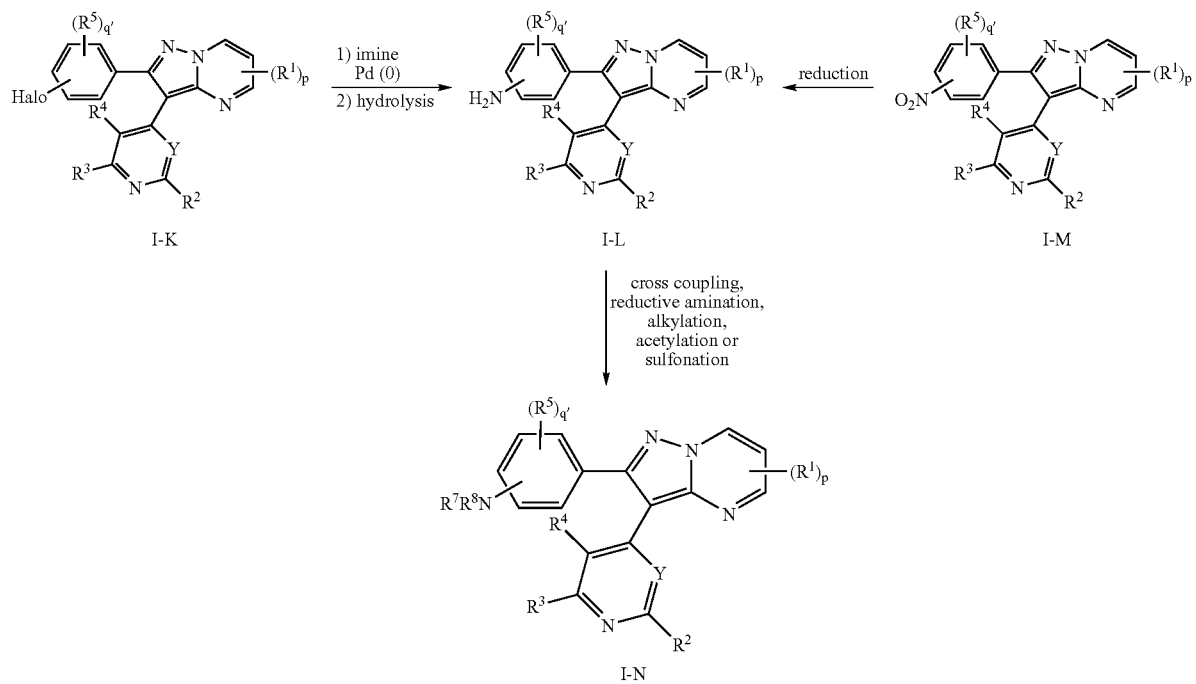

Optionally, a compound of formula (I-H) may be further converted to a compound of formula (I-J) by an alkylation reaction. The alkylation reaction may be carried out by treating a compound of formula (I-H) in suitable solvent with an alkyl halide of formula $R^{10}$-Halo where $R^{10}$ is as defined above, to form another compound of formula (I-J). The reaction is preferably carried out in the presence of a base and with optionally heating to 50-200° C. The reaction may be carried out in solvents such as N,N-dimethylformamide, dimethylsulfoxide and the like. Typically the base is potassium carbonate, cesium carbonate, sodium hydride or the like. Additionally, as will be apparent to those skilled in the art, the alkylation reaction can be carried out under Mitsunobu conditions.

The foregoing reaction methods can also be used to convert a compound of formula (I) wherein at least one $R^1$ is —OMe to a compound of formula (I) wherein at least one $R^1$ is —OH or a compound of formula (I) wherein at least one $R^1$ is —$OR^{10}$. In another embodiment, the foregoing methods are employed to make the same conversion when $R^3$ or $R^4$ is —OMe, to prepare a compound of formula (I) wherein $R^3$ or $R^4$ is —OH or a compound of formula (I) wherein $R^3$ or $R^4$ is —$OR^{10}$.

In yet another example, a compound of formula (I-K) (i.e., a compound of formula (I) wherein q is 1 or more and wherein q' is 1, 2 or 3, and all other variables are as defined above.

The process of converting a compound of formula (I-K) to a compound of formula (I-L) is carried out by reacting a compound of formula (I-K) with an imine in the presence of a palladium (0) source, a base and a suitable ligand, followed by hydrolysis to give a compound of formula (I-L). See J. Wolfe, et al., *Tetrahedron Letters* 38:6367-6370 (1997). Typically the imine is benzophenoneimine, the palladium (0) source is tris(dibenzylideneacetone)dipalladium(0), the base is sodium tert-butoxide and the ligand is racemic-2,2'-bis(diphenylphosphino)-1,1'-binaphthyl. Suitable solvents include N,N-dimethylformamide and the like.

A compound of formula (I-L) can also be obtained from a compound of formula (I-M) by reduction. The reduction can conveniently be carried out by using zinc, tin or iron and acid, by using tin(II)chloride, or by using palladium or platinum catalysts under hydrogen atmosphere in a suitable solvent as will be apparent to those skilled in the art of organic synthesis.

Reaction of a compound of formula (I-L) with a compound of formula $R^7$-halogen in a suitable solvent in the presence of base, optionally with heating may be used to prepare a compound of formula (I-N). Typically the base is triethylamine or pyridine and the solvent is N,N-dimethylformamide and the like.

Additional compounds of formula (I-N) can be obtained by reductive amination of a compound of formula (I-L) with a ketone or aldehyde. See, A. Abdel-Magid, et al., *J. Org. Chem.* 61:3849-3862 (1996). Typically a compound of formula (I-L) is treated with an aldehyde or a ketone in the presence of an acid, such as acetic acid, and a reducing agent, such as sodium triacetoxyborohydride or the like, in an inert solvent such as dichloroethane or the like.

The foregoing reaction methods can also be used to convert a compound of formula (I) wherein at least one $R^1$ is halo to a compound of formula (I) wherein at least one $R^1$ is —$NH_2$ and a compound of formula (I) wherein at least one $R^6$ is —$NR^7R^8$ (where $R^7$ and $R^8$ are not both H). In another embodiment, the foregoing methods are employed to make the same conversion when $R^3$ or $R^4$ is halo, to prepare a compound of formula (I) wherein $R^3$ or $R^4$ is —$NH_2$ or a compound of formula (I) wherein $R^3$ or $R^4$ is —$NR^7R^8$ (where $R^7$ and $R^8$ are not both H).

Other transformations well known to those skilled in the art for use with anilines may be used to convert a compound of formula (I-L) to a compound of formula (I-N).

Based upon this disclosure and the examples contained herein one skilled in the art can readily convert a compound of formula (I) or a pharmaceutically acceptable salt, solvate or physiologically functional derivative thereof into another compound of formula (I), or a pharmaceutically acceptable salt, solvate or physiologically functional derivative thereof.

The present invention also provides radiolabeled compounds of formula (I) and biotinylated compounds of formula (I). Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I).

In one embodiment, the compounds of formula (I) are tritiated.

The radiolabeled compounds of formula (I) and biotinylated compounds of formula (I) are useful in assays for the identification of compounds for the treatment or prophylaxis of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) or the biotinylated compounds of formula (I) to the target protein. More specifically, suitable assay methods will include competition binding assays. The radiolabeled compounds of formula (I) and biotinylated compounds of formula (I) can be employed in assays according to the methods conventional in the art.

The following examples are intended for illustration only and are not intended to limit the scope of the invention in any way, the invention being defined by the claims which follow.

Reagents are commercially available or are prepared according to procedures in the literature. Example numbers refer to those compounds listed in the tables above. $^1$H and $^{13}$C NMR spectra were obtained on Varian Unity Plus NMR spectrophotometers at 300 or 400 MHz, and 75 or 100 MHz respectively. $^{19}$F NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230-400 mesh), and the stated solvent system under pressure. All compounds were characterized as their free-base form unless otherwise stated. On occasion the corresponding hydrochloride salts were formed to generate solids where noted.

EXAMPLE 1

3-(2-Fluoropyridin-4-yl)-2-phenyl-7-pyrrolidin-1-ylpyrazolo[1,5-α]pyrimidine.

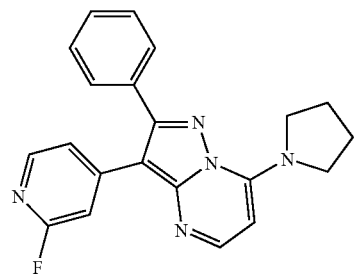

a) 2-Fluoropyridin-4ylboronic Acid.

To a stirred solution of n-butyl lithium (3.2 mL, 2.5M, 8.0 mmol) in dry diethyl ether (20 mL) at −78° C. was added a solution of 2-fluoro-4-iodopyridine (1.5 g, 6.7 mmol) in dry ether (10 mL) and the reaction mixture was stirred at −78° C. for 10 minutes. Tributyl borate (2.4 mL, 2.01 g, 8.7 mmol) was added and the reaction mixture was allowed to warm to room temperature over 2 hours. Water (5 mL) was added followed by 2N aqueous sodium hydroxide solution (10 mL) to dissolve the solids. The organic phase was separated. The aqueous phase was acidified to pH3 using 6N hydrochloric acid and the resulting white solid was collected by filtration and dried under vacuum to give the title compound, 0.74 g (780%). $^1$H NMR (DMSO-d$_6$) δ 8.65 (br s, 2H), 8.21 (d, 1H), 7.59 (t, 1H), 7.37 (d, 1H).

b) 3-Bromo-7-chloro-2-phenylpyrazolo[1,5-α]pyrimidine.

7-Chloro-2-phenylpyrazolo[1,5-α]pyrimidine (0.1 g, 0.44 mmol, prepared as described in J. Med. Chem. 1981, 24, 610) was dissolved in dichloromethane (5 mL) and to this solution was added N-bromosuccinimide (108 mg, 0.61 mmol). The resulting reaction mixture was stirred for 30 minutes. Additional dichloromethane was added and the mixture was extracted with sodium hydroxide (1N), water and a saturated aqueous sodium chloride solution. The organic phase was dried over magnesium sulfate, filtered and concentrated. The resulting solid was purified by silica gel chromatography (ethyl acetate:hexane 1:2) to give 110 mg (82%) of 3-bromo-7-chloro-2-phenylpyrazolo[1,5-α]pyrimidine as a yellow solid.

1H NMR (CDCl$_3$):δ 8.50 (d, 1H), 8.17 (m, 2H), 7.57 (m, 3H), 7.07 (d, 1H); MS m/z 308 (M+1).

c) 3-Bromo-2-phenyl-7-pyrrolidin-1-ylpyrazolo[1,5-α]pyrimidine.

3-Bromo-7-chloro-2-phenylpyrazolo[1,5-α]pyrimidine (100 mg, 0.32 mmol) was dissolved in ethanol. To this solution was added pyrrolidine (0.5 mL) and the reaction mixture heated at reflux for 10 minutes. The resulting mixture was concentrated in vacuo, then dissolved in dichloromethane and the organic phase was washed with water, dried over magnesium sulfate, filtered and concentrated. The resulting solid was crystallized from methanol to give 85 mg (77%) of 3-bromo-2-phenyl-7-pyrrolidin-1-ylpyrazolo[1,5-α]pyrimidine as a solid. $^1$H NMR (CDCl$_3$):δ 8.17 (m, 3H), 7.50 (m, 3H), 5.80 (d, 1H), 4.09 m (broad s, 4H), 2.10 (broad s, 4H); MS m/z 343 (M+1).

d) 3-(2-Fluoropyridin-4-yl)-2-phenyl-7-pyrrolidin-1-ylpyrazolo[1,5-α]pyrimidine.

3-Bromo-2-phenyl-7-pyrrolidin-1-ylpyrazolo[1,5-α]pyrimidine (150 mg, 0.44 mmol) was dissolved in N,N-dimethylformamide (4 mL). To this solution was added dichlorobis(tripenylphosphine)palladium (II) (60 mg, 0.09 mmol), 2-fluoropyridin-4-ylboronic acid (92 mg, 0.66 mmol), sodium carbonate (185 mg, 1.76 mmol) and a few drops of water. The resulting solution was heated at 110° C. for 24 hours. The resulting mixture was diluted with dichloromethane and washed with water. The organic phase was dried over magnesium sulfate, filtered and concentrated. The resulting black residue was purified by silica gel chromatography (ethyl acetate:hexane 1:1) to give 50 mg (32%) of the title compound as a white solid. $^1$H NMR (CDCl$_3$):δ 8.17 (d, 1H), 8.08 (d, 1H), 7.60 (m, 2H), 7.41 (m, 4H), 7.24 (broad s, 1H), 5.87 (d, 1H), 4.06 (broad s, 4H), 2.07 (broad s, 4H); $^{19}$F NMR (CDCl$_3$):δ −69.34; MS m/z 360 (M+1).

EXAMPLE 2

N-Cyclopentyl-4(2-phenyl-7-pyrrolidin-1-ylpyrazolo[1,5-α]pyrimidin-3-yl)pyridin-2-amine and Example 3

N-Cyclopentyl-3-[2-(cyclopentylamino)pyridin-4-yl]-2-phenylpyrazolo[1,5-α]pyrimidin-7-amine

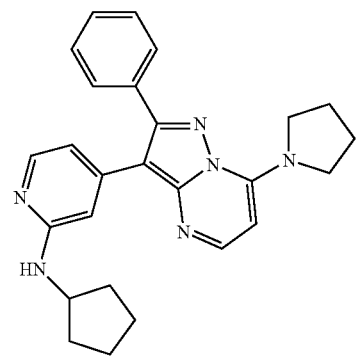

Example 2

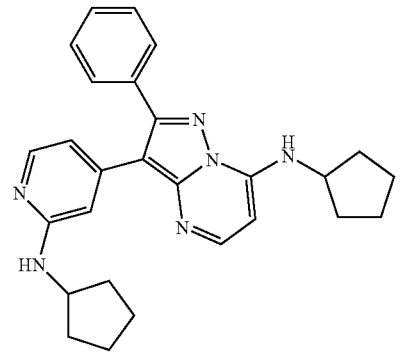

Example 3

3-(2-Fluoropyridin-4yl)-2-phenyl-7-pyrrolidin-1-yl(pyrazolo[1,5-α]pyrimidine (50 mg, 0.14 mmol) was dissolved in cyclcopentylamine (4 mL) and placed in a pressure tube. Reaction was heated to 150° C. overnight, and then to 165° C. for 2 days. Reaction was cooled to room temperature, then concentrated in vacuo to a solid. This solid was purified by silica gel chromatography (ethyl acetate:hexane 1:1) to give 15 mg (25%) of N-cyclopentyl-4-(2-phenyl-7-pyrrolidin-1-ylpyrazolo[1,5-α]pyrimidin-3-yl)pyridin-2-amine as a foam and 4 mg (7%) of N-cyclopentyl-3-[2-(cyclopentylamino)pyridin-4-yl]-2-phenylpyrazolo[1,5-α]pyrimid in-7-amine.

For N-cyclopentyl-4-(2-phenyl-7-pyrrolidin-1-ylpyrazolo[1,5-α]pyrimidin-3-yl)pyridin-2-amine:$^1$H NMR (CDCl$_3$):δ 8.14 (d, 1H), 7.99 (d, 1H), 7.64 (m, 2H), 7.38 (m, 3H), 6.84 (dd, 1H), 6.56 (s, 1H), 5.80 (d, 1H), 4.68 (broad s, 1H), 4.05 (broad s, 4H), 3.77 (m, 1H), 1.3-2.1 (m, 12H); MS m/z 425 (M+1).

For N-cyclopentyl-3-[2-(cyclopentylamino)pyridin-4-yl]-2-phenylpyrazolo[1,5-α]pyrimidin-7-amine: $^1$H NMR (CDCl$_3$):δ 8.30 (d, $_1$H), 8.01 (d, 1H), 7.64 (m, 2H), 7.41 (m, 3H), 6.86 (dd, 1H), 6.56 (s, 1H), 6.43 (d, 1H), 6.05 (d, 1H), 4.54 (m, 1H), 4.08 (m, 1H), 3.77 (m, 1H), 1.3-2.1 (m, 16H); MS m/z 439 (M+1).

EXAMPLE 4

N-Cyclopentyl-3-[2-(cyclopentylamino)-4-pyridinyl]-2-(4-methoxyphenyl)pyrazolo[1,5-α]pyrimidin-7-amine

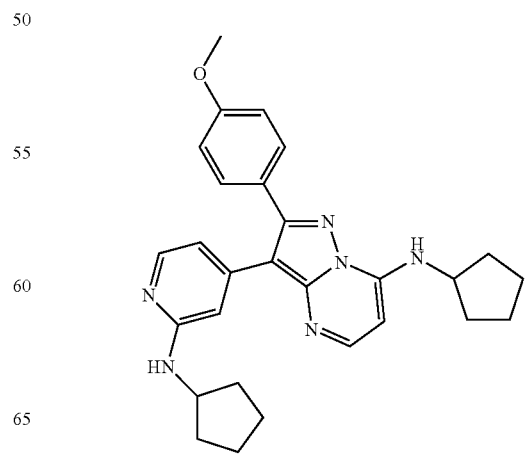

The title compound was prepared in a similar manner as described above to give a tan foam. $^1$H NMR (DMSO-d$_6$) δ 8.19 (d, 1H), 7.80 (d, 1H), 7.68 (d, 1H), 7.52 (d, 2H), 6.99 (d, 2H), 6.68 (s, 1H), 6.47 (d, 1H), 6.39 (br s, 1H), 6.31 (d, 1H), 4.15-4.05 (m, 1H), 3.95-3.88 (m, 1H), 3.78 (s, 3H), 2.1-1.3 (m, 16H); MS m/z 469 (M+1). Anal. Calcd. for C$_{28}$H$_{32}$N$_6$O. 0.3 H$_2$O: C, 70.95; H, 6.93; N, 17.73. Found: C, 70.96; H, 6.91; N, 17.70.

EXAMPLE 5

N-Cyclopentyl-3-[2-(cyclopentylamino)-4-pyridinyl]-2-(4-fluorophenyl)pyrazolo[1,5-α]pyrimidin-7-amine

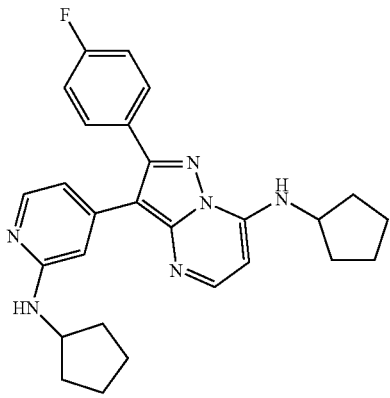

The title compound was prepared in a similar manner as described above to give a tan foam. $^1$H NMR (CDCl$_3$) δ 8.30 (d, 1H), 8.02 (d, 1H), 7.63 (dd, 2H), 7.12 (t, 2H), 6.80 (d, 1 H), 6.55 (s, 1H), 6.39 (d, 1H), 6.05 (d, 1H), 4.55 (br s, 1H), 4.1-4.0 (m, 1H), 3.85-3.75 (m, 1 H), 2.2-1.4 (m, 16H); MS m/z 457 (M+1).

EXAMPLE 6

N-Cyclopentyl-3-[2-(cyclopentylamino)pyrimidin-4-yl]-2-(4-methoxyphenyl)pyrazolo[1,5-α]pyrimidin-7-amine

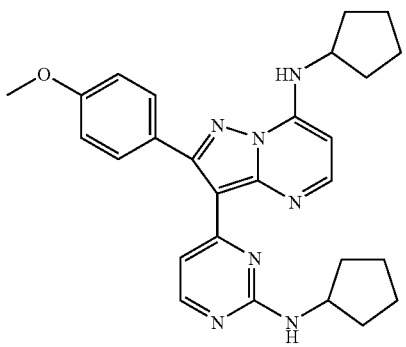

a) N-Cyclopentyl-3-iodo-2-(4-methoxyphenyl)pyrazolo[1,5-α]pyrimidin-7-amine.

To a solution of 7-chloro-2-(4-methoxyphenyl)pyrazolo[1,5-α]pyrimidine (0.25 g, 0.96 mmol) in dichloromethane (8 mL) was added N-iodosuccinimide. The reaction was stirred at room temperature for 2 hours before being diluted with dichloromethane (50 mL). The solution was washed with aqueous 2M sodium hydroxide (50 mL) and concentrated. The residue was dissolved in cyclopentylamine (5 mL) and stirred overnight at room temperature. The mixture was concentrated and the residue purified by silica chromatography, eluting with 5% acetone in dichloromethane to yield 190 mg (45%) of N-cyclopentyl-3-iodo-2-(4-methoxyphenyl)pyrazolo[1,5-α]pyrimidin-7-amine. MS m/z 435 (M+1).

b) 2-(Methylsulfanyl)-4-(tributylstannyl)pyrimidine.

To a solution of 4-iodo-2-(methylsulfanyl)pyrimidine (1.0 g. 4.0 mmol) in tetrahydrofuran (6 ml) was added 1,1,1,2,2,2-hexabutyldistannane (4.1 mL, 8.2 mmol), bis(triphenylphoshine)palladium(III)acetate (0.090 g, 0.12 mmol), and 1M tetrabutylammonium fluoride in tetrahydrofuran (12 mL, 12 mmol). The mixture was stirred for 3 hours at room temperature and concentrated. The residue was taken up in ethyl acetate, washed with water before being dried over magnesium sulfate. The solution was filtered, concentrated and the residue purified by silica chromatography, eluting with 100% ethyl acetate in hexanes to yield 0.34 g (37%) of 2-(methylsulfanyl)-4-(tributylstannyl)pyrimidine. MS m/z 416 (M+1).

c) N-Cyclopentyl-3-[2-(cyclopentylamino)pyrimidin-4yl]-2-(4-methoxyphenyl)pyrazolo[1,5-α]pyrimidin-7-amine.

N-Cyclopentyl-3-iodo-2-(4-methoxyphenyl)pyrazolo[1,5-α]pyrimidin-7-amine (63 mg, 0.15 mmol), dichlorobis(triphenylphosphine)palladium(II) (25 mg, 0.015 mmol), and 2-(methylsulfanyl)-4-(tributylstannyl)pyrimidine (78 mg, 0.19 mmol) were added to toluene (3 mL) and heated to 110° C. for 16 hours. Additional dichlorobis(triphenylphosphine)palladium(II) (6 mg) was added and the reaction heated to 110° C. for 24 hours. The reaction was allowed to cool to room temperature, diluted with ethyl acetate, poured into 10% aqueous potassium fluoride containing 1% methanol, and stirred for 20 minutes before being extracted with ethyl acetate. The organic phase was concentrated and the residue purified by silica chromatography, eluting with a gradient of 5% to 10% acetone in dichloromethane to yield 25 mg of an approximate 1:1 mixture of N-cyclopentyl-2-(4-methoxyphenyl)pyrazolo[1,5-α]pyrimidin-7-amine and N-cyclopentyl-2-(4-methoxyphenyl)-3-[2-(methylsulfanyl)pyrimidin-4yl]pyrazolo[1,5-α]pyrimidin-7-amine. To a 0° C. solution of this mixture in dichloromethane (1 mL) was added 3-chloroperoxybenzoic acid (0.099 mg, 0.058 mmol). The mixture was allowed to warm to room temperature and stirred for 2 hours. The mixture was diluted with dichloromethane, washed with saturated aqueous sodium bicarbonate, and concentrated. The residue was dissolved in cyclopentylamine and stirred at room temperature for 2.5 hours. The mixture was concentrated and the residue purified by silica chromatography, eluting with a gradient of 5% to 15% acetone in dichloromethane to yield 14 mg (11%) of N-cyclopentyl-3-[2-(cyclopentylamino)pyrimidin-4-yl]-2-(4methoxyphenyl)pyrazolo[1,5-α]pyrimidin-7-amine. $^1$H NMR (CDCl$_3$):δ 8.37 (d, 1H), 8.26 (d, 1H), 7.67 (d, 2H), 6.99 (d, 2H), 6.50 (d, 1H), 6.11 (d, 1H), 5.01 (m, 1H), 4.09 (m, 1H), 3.90 (s, 3H), 2.20 (m, 2H), 1.75 (m, 14H); MS m/z 470 (M+1).

EXAMPLE 7

Biological Activity

In the following example, "MEM" means Minimal Essential Media; "FBS" means Fetal Bovine Serum; "NP40" and "Igepal" are detergents; "MOI" means Multiplicity of Infection; "NaOH" means sodium hydroxide; "MgCl$_2$" means magnesium chloride; "dATP" means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "TE" means Tris-EDTA; "SCC" means sodium chloride/sodium citrate; "APE" means a solution of ammonia acetate, ammonia phosphate, EDTA; "PBS" means phosphate buffered saline; and "HRP" means horseradish peroxidase.

a) Tissue Culture and HSV Infection.

Vero 76 cells were maintained in MEM with Earle's salts, L-glutamine, 8% FBS (Hyclone, A-1111-L) and 100 units/mL Penicillin-100 µg/mL Streptomycin. For assay conditions, FBS was reduced to 2%. Cells are seeded into 96-well tissue culture plates at a density of 5×10$^4$ cells/well after being incubated for 45 min at 37° C. in the presence of HSV-1 or HSV-2 (MOI=0.001). Test compounds are added to the wells and the plates are incubated at 37° C. for 40-48 hours. Cell lysates are prepared as follows: media was removed and replaced with 150 µL/well 0.2 N NaOH with 1% igepal CA 630 or NP-40. Plates were incubated up to 14 days at room temperature in a humidified chamber to prevent evaporation.

(b) Preparation of detection DNA.

For the detection probe, a gel-purified, digoxigenin-labeled, 710-bp PCR fragment of the HSV UL-15 sequence was utilized. PCR conditions included 0.5 µM primers, 180 µM dTTP, 20 µM dUTP-digoxigenin (Boehringer Mannheim 1558706), 200 µM each of dATP, dCTP, and dGTP, 1× PCR Buffer II (Perkin Elmer), 2.5 mM MgCl$_2$, 0.025 units/µL of AmpliTaq Gold polymerase (Perkin Elmer), and 5 ng of gel-purified HSV DNA per 100 µL Extension conditions were 10 min at 95° C., followed by 30 cycles of 95° C. for 1 min, 55° C. for 30 sec, and 72° C. for 2 min. The amplification was completed with a 10-min incubation at 72° C. Primers were selected to amplify a 728 bp probe spanning a section of the HSV1 UL15 open reading frame (nucleotides 249-977). Single-stranded transcripts were purified with Promega M13 Wizard kits. The final product was mixed 1:1 with a mixture of 6 M GuSCN, 100 mM EDTA and 200 µg/mL herring sperm DNA and stored at 4° C.

(c) Preparation of Capture Plates.

The capture DNA plasmid (HSV UL13 region in pUC) was linearized by cutting with Xba I, denatured for 15 min at 95° C. and diluted immediately into Reacti-Bind DNA Coating Solution (Pierce, 17250, diluted 1:1 with TE buffer, pH 8) at 1 ng/µL. 75 µL/well were added to Corning (#3922 or 9690) white 96-well plates and incubated at room temperature for at least 4 hrs before washing twice with 300 µL/well 0.2×SSC/0.05% Tween-20 (SSC/T buffer). The plates were then incubated overnight at room temperature with 150 µL/well 0.2 N NaOH, 1% IGEPAL and 10 µg/mL herring sperm DNA.

(d) Hybridization.

Twenty-seven (27) µL of cell lysate was combined with 45 µL of hybridization solution (final concentration: 3M GuSCN, 50 mM EDTA, 100 µg/ml salmon sperm DNA, 5× Denhardt's solution, 0.25× APE, and 5 ng of the digoxigenin-labeled detection probe). APE is 1.5 M NH$_4$-acetate, 0.15 M NH$_4$H$_2$ phosphate, and 5 mM EDTA adjusted to pH 6.0. Mineral oil (50 µL) was added to prevent evaporation. The hybridization plates were incubated at 95° C. for 10 minutes to denature the DNA, then incubated at 42° C. overnight. The wells were washed 6× with 300 µL/well SSC/T buffer then incubated with 75 µL/well anti-digoxigenin-HRP-conjugated antibody (Boehringer Mannheim 1207733, 1:5000 in TE) for 30 min at room temperature. The wells were washed 6× with 300 µL/well with PBS/0.05% Tween-20 before 75 µL/well SuperSignal LBA substrate (Pierce) was added. The plates were incubated at room temperature for 30 minutes and chemiluminescence was measured in a Wallac Victor reader.

e) Results.

The following results were obtained for HSV-1.

| Example No. | IC$_{50}$ (µM) |
|---|---|
| 1 | 28 |
| 2 | 0.8 |
| 3 | 0.3 |
| 4 | 0.6 |
| 5 | 1.2 |
| 6 | 2.4 |

The results demonstrate that the compounds of the present invention are useful for the treatment and prophylaxis of herpes viral infections.

The invention claimed is:
1. A compound of formula (I):

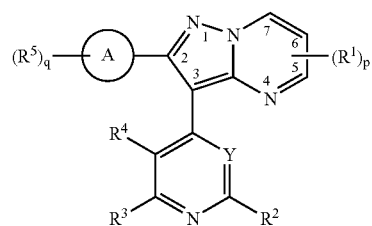

wherein:

p is 1, 2 or 3;

each R$^1$ is the same or different and is independently selected from the group consisting of halo, alkyl, alkenyl, alkynyl, cycloalkyl, cycloalkenyl, Ay, Het, —C(O)R$^9$, —C(O)Ay, —C(O)Het, —CO$_2$R$^9$, —C(O)NR$^7$R$^8$, —C(O)NR$^7$Ay, —C(S)NR$^9$R$^{11}$, —C(NH)NR$^7$R$^8$, —C(NH)NR$^7$Ay, —OR$^7$, —OAy, —OHet —OR$^{10}$Ay, —OR$^{10}$Het, —NR$^7$R$^8$, —NR$^7$Ay, —NH-Het, —NHR$^{10}$Ay, —NHR$^{10}$Het, —S(O)$_n$R$^9$, —S(O)$_n$Ay, —S(O)$_n$Het, —S(O)$_2$NR$^7$R$^8$, —S(O)$_2$NR$^7$Ay, —R$^{10}$cycloalkyl, —R$^{10}$Ay, —R$^{10}$OR$^9$, —R$^{10}$NR$^7$R$^8$, —R$^{10}$NR$^7$Ay, —R$^{10}$NHSO$_2$R$^9$, —R$^{10}$C(O)R$^9$, —R$^{10}$C(O)Ay, —R$^{10}$C(O)Het, —R$^{10}$CO$_2$R$^9$, —R$^{10}$OC(O)R$^9$, —R$^{10}$OC(O)Ay, —R$^{10}$OC(O)Het, —R$^{10}$C(O)NR$^9$R$^{11}$, —R$^{10}$C(O)NR$^7$Ay, —R$^{10}$C(O)NHR$^{10}$Het, —R$^{10}$C(S)NR$^9$R$^{11}$, —R$^{10}$C(NH)NR$^9$R$^{11}$, —R$^{10}$SO$_2$R$^9$, —$R^{10}SO_2NR^9R^{11}$, —$R^{10}SO_2NHCOR^9$, —$R^{10}OS(O)_n$ $R^9$, cyano, nitro and azido;

- each $R^7$ and $R^8$ are the same or different and are independently selected from the group consisting of H, alkyl, cycloalkyl, alkenyl, cycloalkenyl, —C(O) $R^9$, —$CO_2R^9$, —$C(O)NR^9R^{11}$, —$C(S)NR^9R^{11}$, —$C(NH)NR^9R^{11}$, —$SO_2R^{12}$, —$SO_2NR^9R^{11}$, —$R^{10}$cycloalkyl, —$R^{10}C(O)R^9$, —$R^{10}CO_2R^9$, —$R^{10}C(O)NR^9R^{11}$, —$R^{10}C(S)NR^9R^{11}$, —$R^{10}OR^9$, —$R^{10}NR^9R^{11}$, —$R^{10}NHCOR^9$, —$R^{10}NHC(NH)NR^9R^{11}$, —$R^{10}C(NH)NR^9R^{11}$, —$R^{10}NHSO_2R^9$, —$R^{10}SO_2NR^9R^{11}$, —$R^{10}SO_2R^{12}$ and —$R^{10}SO_2NHCOR^9$;
- each $R^9$ and $R^{11}$ are the same or different and are independently selected from the group consisting of H, alkyl, cycloalkyl, —$R^{10}$cycloalkyl, —$R^{10}OH$, —$R_{10}(OR^{12})_w$ where w is 1-10, and —$R^{10}NR^{12}R^{12}$;

"$R^{10}$ is the same or different and is independently selected from the group consisting of alkylene, cycloalkylene, alkenylene, cycloalkenylene, and alkynylene;" each $R^{12}$ is the same or different and is independently selected from the group consisting of alkyl, cycloalkyl, alkenyl, cycloalkenyl, and alkynyl;

Ay is aryl;

Het is a 5- or 6-membered heterocyclic or heteroaryl group;

n is 0, 1 or 2;

Y is N or CH;

$R^2$ is selected from the group consisting of Ay, Het, —OAy, —OHet, —$OR^{10}Ay$, —$OR^{10}Het$, —$NR^7R^8$, —$NR^7Ay$, —NHHet, —$NHR^{10}Ay$, —$NHR^{10}Het$, —$S(O)_nR^9$, —$S(O)_nAy$, —$R^{10}NR^7R^8$ and —$R^{10}NR^7Ay$;

$R^3$ and $R^4$ are the same or different and are each independently selected from the group consisting of H, halo, alkyl, alkenyl, cycloalkyl, Ay, Het, —$C(O)R^7$, —C(O)Ay, —$CO_2R^7$, —$CO_2Ay$, —$OR^7$, —OAy, —$OR^{10}Ay$, —$OR^{10}Het$, —$NR^7R^8$, —$NR^7Ay$, —NHHet, —$SO_2NHR^9$, —$R^{10}OR^7$, —$R^{10}$cycloalkyl, —$R^{10}OAy$, —$R^{10}NR^7R^8$ and —$R^{10}NR^7Ay$;

Ring A is selected from the group consisting of aryl, 5-10 membered heterocyclic group and a 5-10 membered heteroaryl group;

q is 0, 1, 2, 3, 4 or 5; and each $R^5$ is the same or different and is independently selected from the group consisting of halo, alkyl, alkenyl, alkynyl, cycloalkyl, cycloalkenyl, Ay, Het, —$C(O)R^9$, —C(O)Ay, —C(O)Het, —$CO_2R^9$, —C(O) $NR^7R^8$, —$C(O)NR^7Ay$, —$C(S)NR^9R^{11}$, —C(NH) $NR^7R^8$, —$C(NH)NR^7Ay$, —$OR^7$, —OAy, —OHet, —$OR^{10}Ay$, —$OR^{10}Het$, —$NR^7R^8$, —$NR^7Ay$, —NHHet, —$NHR^{10}Ay$, —$NHR^{10}Het$, —$S(O)_nR^9$, —$S(O)_2NR^7R^8$, —$S(O)_2NR^7Ay$, —$R^{10}$cycloalkyl, —$R^{10}Het$, —$R^{10}C(O)R^9$, —$R^{10}CO_2R^9$, —$R^{10}C(O)NR^9R^{11}$, —$R^{10}C(O)NR^7Ay$, —$R^{10}C(O)NHR^{10}Het$, —$R^{10}C(S)NR^9R^{11}$, —$R^{10}C(NH)NR^9R^{11}$, —$R^{10}OR^9$, —$R^{10}NR^7R^8$, —$R^{10}NR^7Ay$, —$R^{10}SO_2R^9$, —$R^{10}SO_2NR^9R^{11}$, —$R^{10}SO_2NHCOR^9$, cyano, nitro and azido;

or a pharmaceutically acceptable salt, thereof.

2. The compound according to claim 1 wherein each $R^1$ is the same or different and is independently selected from the group consisting of halo, alkyl, alkenyl, alkynyl, cycloalkyl, cycloalkenyl, Ay, Het, —$OR^7$, —OAy, —OHet, —$OR^{10}Ay$, —$OR^{10}Het$, —$NR^7R^8$, —$NR^7Ay$, —NHHet, —$NHR^{10}Ay$, —$NHR^{10}Het$, —$S(O)_nR^9$, —$S(O)_nAy$, —$S(O)_n$Het, —$S(O)_2NR^7R^8$, —$S(O)_2NR^7Ay$, cyano, nitro and azido.

3. The compound according to claim 1 wherein each $R^1$ is the same or different and is independently selected from the group consisting of halo, Ay, Het and —$NR^7R^8$.

4. The compound according to claim 1 wherein p is 1.

5. The compound according to claim 1 wherein Y is OH.

6. The compound according to claim 1 wherein Y is N.

7. The compound according to claim 1 wherein $R^2$ is selected from the group consisting of Het, —$NR^7R^8$, —$NR^7Ay$, —NHHet and —$S(O)_nR^9$.

8. The compound according to claim 1 wherein $R^2$ is selected from the group consisting of Het and —$NR^7R^8$.

9. The compound according to claim 1 wherein $R^3$ and $R^4$ are the same or different and are each independently selected from the group consisting of H, halo, alkyl, Ay, —$OR^7$, —$CO_2R^7$, —$NR^7R^8$, —$R^{10}OR^7$ and —$R^{10}NR^7R^8$.

10. The compound according to claim 1 wherein $R^3$ and $R^4$ are both H.

11. The compound according to claim 1 wherein Ring A is selected from the group consisting of aryl, a 5-6 membered heterocyclic or heteroaryl group and a 9-membered heterocyclic or heteroaryl group.

12. The compound according to claim 1 wherein Ring A is selected from the group consisting of phenyl, naphthyl, furan, pyridine, pyrimidine, thiazole, pyrazine, pyrrole, imidazole, oxazole, berizimidazole, quinoline, isoquinoline and quinoxoline.

13. The compound according to claim 1 wherein Ring A is selected from the group consisting of phenyl, furan, pyridine and pyrimidine.

14. The compound according to claim 1 wherein Ring A is phenyl.

15. The compound according to claim 1 wherein q is 0,1 or 2.

16. The compound according to claim 1 wherein each $R^5$ is the same or different and is independently selected from the group consisting of halo, alkyl, alkenyl, Ay, Het, —$CO_2R^9$, —$C(O)NR^7R^8$, —$OR^7$, —OAy, —$NR^7R^8$, —$NR^7Ay$, —$S(O)_2NR^7R^8$, cyano, nitro and azido.

17. The compound according to claim 1, wherein each $R^5$ is the same or different and is independently selected from the group consisting of halo, alkyl, —$OR^7$, —$NR^7R^8$ and cyano.

18. A compound selected from the group consisting of:
3-(2-Fluoropyridin-4-yl)-2-phenyl-7-pyrrolidin-1-yl pyrazolo[1,5-α]pyrimidine;

N-Cyclopentyl-4-(2-phenyl-7-pyrrolidin-1-ylpyrazolo[1, 5-α]pyrimidin-3-yl )pyridin-2-amine;

N-Cyclopentyl-3-[2-(cyclopentylamino)pyridin-4-yl]-2-phenyl pyrazolo[1,5-α]pyrimidin-7-amine;

N-Cyclopentyl-3-[2-(cyclopentylamino)-4-pyridinyl]-2-(4-methoxyphenyl)pyrazolo[1,5-α]pyrimidin-7-amine;

N-Cyclopentyl-3-[2-(cyclopentylamino)-4-pyridinyl-]-2-(4-fluorophenyl)pyrazolo[1,5-α]pyrimidin-7-amine; and N-Cycloperltyl-3-[2-(cyclopentylamino)pyrimidin-4-yl]-2-(4-methoxyphenyl)pyrazolo[15-α]pyrimidin-7-amine, or a pharmaceutically acceptable salt, thereof.

19. A pharmaceutical composition comprising a compound according to claim 1 and a pharmaceutically acceptable carrier or diluent.

20. A method for the treatment of a herpes viral infection selected from herpes simplex virus 1 and herpes simplex virus 2, in an animal, said method comprising administering to the animal a therapeutically effective amount of a compound according to claim 1.

21. A process for preparing a compound according to claim 1 comprising reacting the compound of formual (VII-A):

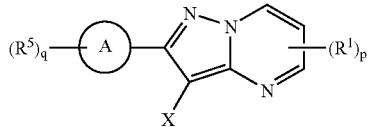

VII-A wherein X is chloro, bromo or iodo;
with a compound of formula (VIII):

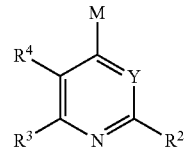

VIII wherein M is selected from the group consisting of —B(OH)$_2$, —B(ORa)$_2$, —B(Ra)$_2$, —Sn(Ra)$_3$, Zn-halide, ZnRa, Mg-halide where Ra is alkyl or cycloalkyl and halide is halo;
to prepare a compound of formula (I).

* * * * *

UNITED STATES PATENT AND TRADEMARK OFFICE
CERTIFICATE OF CORRECTION

| | |
|---|---|
| PATENT NO. | : 7,304,068 B2 |
| APPLICATION NO. | : 10/512916 |
| DATED | : December 4, 2007 |
| INVENTOR(S) | : Gudmundsson et al. |

It is certified that error appears in the above-identified patent and that said Letters Patent is hereby corrected as shown below:

Column 39, Claim 1, line 18 should read:
--$R^{10}$ is the same or different and is independently--

Column 39, Claim 1, line 21 should read:
--alkynylene; each $R^{12}$ is the same or different and is--

Column 40, Claim 5, line 8 should read:
--5. The compound according to claim 1 wherein Y is CH.--

Column 40, Claim 12, line 28 should read:
--dazole, oxazole, benzimidazole, quinoline, isoquinoline and--

Column 40, Claim 15, line 35, should read:
--15. The compound according to claim 1 wherein q is 0, 1--

Column 40, Claim 16, line 42 should read:
-- -$NR^7Ay$, -$S(O)_2NR^7R^8$, cyano, nitro and azido.--

Column 40, Claim 18, line 56 should read:
--N-Cyclopentyl-3-[2-(cyclopentylamino)-4-pyridinyl]-2- --

Column 40, Claim 18, line 59 should read:
--N-Cyclopentyl-3-[2-(cyclopentylamino)pyrimidin-4-yl]--

UNITED STATES PATENT AND TRADEMARK OFFICE
CERTIFICATE OF CORRECTION

PATENT NO. : 7,304,068 B2
APPLICATION NO. : 10/512916
DATED : December 4, 2007
INVENTOR(S) : Gudmundsson et al.

It is certified that error appears in the above-identified patent and that said Letters Patent is hereby corrected as shown below:

Column 40, Claim 18, line 60 should read:
--2-(4-methoxyphenyl)pyrazolo[1,5-α]pyrimidin-7- --

Signed and Sealed this

Tenth Day of June, 2008

JON W. DUDAS
*Director of the United States Patent and Trademark Office*